US010342838B2

(12) United States Patent
Ozga et al.

(10) Patent No.: US 10,342,838 B2
(45) Date of Patent: Jul. 9, 2019

(54) **PEA (*PISUM SATIVUM* L.) SEED COATS AND SEED COAT FRACTIONS**

(71) Applicant: The Governors of the University of Alberta, Edmonton (CA)

(72) Inventors: Jocelyn Ozga, Edmonton (CA); Catherine Chan, Edmonton (CA); Alena Jin, Edmonton (CA); Han Yang, Edmonton (CA); Seyede Zohre Hashemi, Edmonton (CA); Kaiyuan Yang, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 75 days.

(21) Appl. No.: 14/833,355

(22) Filed: Aug. 24, 2015

(65) Prior Publication Data

US 2016/0058813 A1 Mar. 3, 2016

Related U.S. Application Data

(60) Provisional application No. 62/041,277, filed on Aug. 25, 2014.

(51) Int. Cl.
*A61K 36/00* (2006.01)
*A61K 36/48* (2006.01)

(52) U.S. Cl.
CPC .................................. *A61K 36/48* (2013.01)

(58) Field of Classification Search
CPC ..................................................... A61K 36/00
USPC ......................................................... 424/725
See application file for complete search history.

(56) References Cited

U.S. PATENT DOCUMENTS

| | | | | | |
|---|---|---|---|---|---|
| 4,181,747 A | * | 1/1980 | Kickle | ...................... | A21D 2/36 426/431 |
| 4,774,096 A | * | 9/1988 | Nickel | ................... | A21D 13/02 127/37 |
| 4,824,683 A | * | 4/1989 | Hodgson | ................ | A21D 13/02 426/550 |
| 7,763,292 B2 | * | 7/2010 | Gutierrez-Uribe | .... | A61K 36/48 424/44 |

FOREIGN PATENT DOCUMENTS

| CN | 102783524 | * 11/2012 | |
| CN | 102783524 A | 11/2012 | |

OTHER PUBLICATIONS

Gu et al., The Journal of Nutrition, 22 pages, 2004.*
Shaoping Deng et al., "Structural and Functional Abnormalities in the Islets Isolated From Type 2 Diabetic Subjects," Diabetes, Mar. 2004, pp. 624-632, vol. 53, No. 3, American Diabetes Association.
A. Clark et al., "Islet amyloid, increased A-cells, reduced B-cells and exocrine fibrosis: quantitative changes in the pancreas in type 2 diabetes," Diabetes Research, Apr. 1988, pp. 151-159, vol. 9, Teviot-Kimpton Publications.
Jan A. Ehses et al., "Pancreatic islet inflammation in type 2 diabetes: from α and β cell compensation to dysfunction," Archives of Physiology and Biochemistry, Oct. 2009, pp. 240-247, vol. 115, No. 4, Informa.
Ivan Quesada et al., "Physiology of the pancreatic α-cell and glucagon secretion: role in glucose homeostasis and diabetes," Journal of Endocrinology, Oct. 2008, pp. 5-19, vol. 199, Society for Endocrinology, Great Britain.
S. Dinneen et al., "Failure of glucagon suppression contributes to postprandial hyperglycaemia in IDDM," Diabetologia, Mar. 1995, pp. 337-343, vol. 38, No. 3, Springer-Verlag.
Kiran S. Panickar, "Effects of dietary polyphenols on neuroregulatory factors and pathways that mediate food intake and energy regulation in obesity," Molecular Nutrition & Food Research, Jan. 2013, pp. 34-47, vol. 57, No. 1, Wiley-VCH.
Tia M. Rains et al., "Antiobesity effects of green tea catechins: a mechanistic review," Journal of Nutritional Biochemistry, Jan. 2011, pp. 1-7, vol. 22, No. 1, Elsevier.
Manal M. Abd El Mohsen et al., "Uptake and Metabolism of Epicatechin and Its Access to the Brain After Oral Ingestion," Dec. 2002, pp. 1,693-1,702, vol. 33, No. 12, Elsevier.
Elas M. Janle et al, "Pharmacokinetics and Tissue Distribution of 14C-Labeled Grape Polyphenols in the Periphery and the Central Nervous System Following Oral Administration," Journal of Medicinal Food, Aug. 2010, pp. 926-933, vol. 13, No. 4, Mary Ann Liebert, Inc.
Jun Wang et al., "Brain-Targeted Proanthocyanidin Metabolites for Alzheimer's Disease Treatment," The Journal of Neuroscience, Apr. 11, 2012, pp. 5,144-5,150, vol. 32, No. 15, The Authors.
Michelle C. Venables et al., "Green tea extract ingestion, fat oxidation, and glucose tolerance in healthy humans," American Journal of Clinical Nutrition, Mar. 2008, pp. 778-784, vol. 87, No. 3, American Society for Nutrition.
Adrian B. Hodgson et al., "The Effect of Green Tea Extract on Fat Oxidation at Rest and during Exercise: Evidence of Efficacy and Proposed Mechanisms," Advances in Nutrition, Mar. 2013, pp. 129-140, vol. 4, No. 2, American Society for Nutrition.
Rebecca K. Randell et al., "No Effect of 1 or 7 d of Green Tea Extract Ingestion on Fat Oxidation during Exercise," Medicine & Science in Sports & Exercise, May 2013, pp. 883-891, vol. 45, No. 5, American College of Sports Medicine.
Jonatan Ahrén et al., "Increased β-cell volume in mice fed a high-fat diet: A dynamic study over 12 months," Islets, Nov. 1, 2010, pp. 353-356, vol. 2, issue 6, Landes Bioscience.
Giovana Ermetice De Almeida Costa et al., "Chemical composition, dietary fibre and resistant starch contents of raw and cooked pea, common bean, chickpea and lentil legumes," Food Chemistry, Feb. 2006, pp. 327-330, vol. 94, issue 3, Elsevier.
N. Babio et al, "Dietary fibre: influence on body weight, glycemic control and plasma cholesterol profile," Nutricion Hospitalaria, Jun. 2010, pp. 327-340, vol. 25. No. 3.

(Continued)

*Primary Examiner* — Michael V Meller
(74) *Attorney, Agent, or Firm* — S. Serge Shahinian

(57) ABSTRACT

The present disclosure embraces methodology and compositions for preparing pea seed coat fractions conferring improved health and/or other beneficial effects, and such fractions may be used in a human and/or animal diet.

6 Claims, 19 Drawing Sheets

Specification includes a Sequence Listing.

(56) References Cited

OTHER PUBLICATIONS

Canadian Diabetes Association Clinical Practice Guidelines Expert Committee, "Canadian Diabetes Association 2008 clinical practice guidelines for the prevention and management of diabetes in Canada," Canadian Journal of Diabetes, Sep. 2008, vol. 32, supplement 1.

Manisha Chandalia et al., "Beneficial Effects of High Dietary Fiber Intake in Patients With Type 2 Diabetes Mellitus," The New England Journal of Medicine, May 11, 2000, pp. 1,392-1,398, vol. 342, No. 19, Massachusetts Medical Society.

Patrice D. Cani et al., "Interplay between obesity and associated metabolic disorders: new insights into the gut microbiota," Current Opinion in Pharmacology, Dec. 2009, pp. 737-743, vol. 9, No. 6, Elsevier.

P.J.D. Delhanty et al., "Ghrelin and glucose homeostasis," Peptides, Nov. 2011, pp. 2,309-2,318, vol. 32, No. 11, Elsevier.

Montserrat Dueñas et al., "Occurrence of phenolic compounds in the seed coat and the cotyledon of peas (Pisum sativum L.)," European Food Research and Technology, Jun. 16, 2004, pp. 116-123, vol. 219, No. 2, Springer-Verlag.

Kistin R. Freeland et al., "Adaptation of colonic fermentation and glucagon-like peptide-1 secretion with increased wheat fibre intake for 1 year in hyperinsulinaemic human subjects," British Journal of Nutrition, Jan. 2010, pp. 82-90, vol. 103, No. 1, The Authors.

Milagros Galisteo et al., "Effects of dietary fibers on disturbances clustered in the metabolic syndrome," Journal of Nutritional Biochemistry, Feb. 2008, pp. 71-84, vol. 19, No. 2, Elsevier.

J. S. Goodlad et al., "Digestion of complex carbohydrates and large bowel fermentation in rats fed on raw and cooked peas (Pisum sativum)," British Journal of Nutrition, May 1992, pp. 475-488, vol. 67, No. 3, Great Britain.

Martin O. Weickert et al., "Metabolic Effects of Dietary Fiber Consumption and Prevention of Diabetes," The Journal of Nutrition, Mar. 2008, pp. 439-442, vol. 138, No. 3, American Society for Nutrition.

R.L. Hull et al., "Dietary-fat-induced obesity in mice results in beta cell hyperplasia but not increased insulin release: evidence for specificity of impaired beta cell adaptation," Diabetologia, Jun. 4, 2005, pp. 1,350-1,358, vol. 48, No. 7, Springer-Verlag.

David J.A. Jenkins et al., "Viscous and nonviscous fibres, nonabsorbable and low glycaemic index carbohydrates, blood lipids and coronary heart disease," Current Opinion in Lipidology, Feb. 2000, pp. 49-56, vol. 11, No. 1, Lippincott Williams & Wilkins.

Wook Kim et al., "The Role of Incretins in Glucose Homeostasis and Diabetes Treatment," Pharmacological Reviews, Dec. 2008, pp. 470-512, vol. 60, No. 4, National Institute on Aging/National Institutes of Health, USA.

Tatjana Kutoš et al., "Dietary fibre content of dry and processed beans," Food Chemistry, Feb. 2003, pp. 231-235, vol. 80, issue 2, Elsevier.

Zhuo Liu et al., "Insulin and Glucagon Regulate Pancreatic $\alpha$-Cell Proliferation," PLoS ONE, Jan. 25, 2011, vol. 5, issue 1, National Institute on Aging/National Institutes of Health, USA.

Zx Lu et al., "Arabinoxylan fibre improves metabolic control in people with Type II diabetes," European Journal of Clinical Nutrition, Apr. 2004, pp. 621-628, vol. 58, No. 4, Nature Publishing Group.

Marianne S.H. Lunde et al., "Variations in Postprandial Blood Glucose Responses and Satiety after Intake of Three Types of Bread," Journal of Nutrition and Metabolism, May 2011, Hindawi Publishing Corporation.

Zhen Ma et al., "Thermal processing effects on the functional properties and microstructure of lentil, chickpea, and pea flours," Food Research International, Oct. 2011, pp. 2,534-2,544, vol. 44, issue 8, Elsevier.

Emanuele Marconi et al., "Physicochemical, Nutritional, and Microstructural Characteristics of Chickpeas (Cicer arietinum L.) and Common Beans (Phaseolus vulgaris L.) Following Microwave Cooking," Journal of Agricultural and Food Chemistry, Dec. 2000, pp. 5,986-5,994, vol. 48, No. 12, American Chemical Society.

Christopher P. F. Marinangeli et al., "Whole and fractionated yellow pea flours reduce fasting insulin and insulin resistance in hypercholesterolaemic and overweight human subjects," British Journal of Nutrition, Jan. 2011, pp. 110-117, vol. 105, No. 1, The Authors.

Christopher Marinangeli et al., "Whole and fractionated yellow pea flours modulate insulin, glucose, oxygen consumption, and the caecal microbiome in Golden Syrian hamsters," Applied Physiology Nutrition and Metabolism, Dec. 2011, pp. 811-820, vol. 36, No. 6, NRC Research Press.

Stefan P. Massimino et al., "Fermentable Dietary Fiber Increases GLP-1 Secretion and Improves Glucose Homeostasis Despite Increased Intestinal Glucose Transport Capacity in Healthy Dogs," The Journal of Nutrition, Oct. 1998, pp. 1,786-1,793, vol. 128, No. 10, American Society for Nutritional Sciences.

Jill A. Parnell et al., "Prebiotic fibres dose-dependently increase satiety hormones and alter Bacteroidetes and Firmicutes in lean and obese JCR:LA-cp rats," British Journal of Nutrition, Feb. 2012, pp. 601-613, vol. 107, No. 4, PubMed Central Canada.

Anthony Pick et al., "Role of Apoptosis in Failure of $\beta$-Cell Mass Compensation for Insulin Resistance and $\beta$-Cell Defects in the Male Zucker Diabetic Fatty Rat," Diabetes, Mar. 1998, pp. 358-364, vol. 47, No. 3.

Martin O. Weickert et al., "Cereal Fiber Improves Whole-Body Insulin Sensitivity in Overweight and Obese Women," Diabetes Care, Apr. 2006, pp. 775-780, vol. 29, No. 4.

Raylene A. Reimer et al., "Satiety Hormone and Metabolomic Response to an Intermittent High Energy Diet Differs in Rats Consuming Long-Term Diets High in Protein or Prebiotic Fiber," Journal of Proteome, Aug. 2012, pp. 4,065-4,074, vol. 11, No. 8, ACS Publications.

Gertrud Schäfer et al., "Comparison of the effects of dried peas with those of potatoes in mixed meals on postprandial glucose and insulin concentrations in patients with type 2 diabetes," American Journal of Nutrition, Jul. 2003, pp. 99-103, vol. 78, No. 1, American Society for Clinical Nutrition.

Simon Schenk et al., "Different glycemic indexes of breakfast cereals are not due to glucose entry into blood but to glucose removal by tissue," American Journal of Nutrition, Oct. 2003, pp. 742-748, vol. 78, No. 4, American Society for Clinical Nutrition.

Yutaka Seino et al., "GIP and GLP-1, the two incretin hormones: Similarities and differences," Journal of Diabetes Investigation, Feb./Apr. 2010, pp. 8-23, vol. 1, issue 1-2, Asian Association for the Study of Diabetes and Blackwell Publishing Asia Pty Ltd.

J.L. Sievenpiper et al., "Effect of non-oil-seed pulses on glycaemic control: a systematic review and meta-analysi of randomised controlled experimental trials in people with and without diabetes," Diabetologia, Jun. 13, 2009, pp. 1,479-1,1495, vol. 52, No. 8, Springer-Verlag.

Joshua Tarini et al., "The fermentable fibre inulin increases postprandial serum short-chain fatty acids and reduces free-fatty acids and ghrelin in healthy subjects," Applied Physiology, Nutrition, and Metabolism, Jan. 20, 2010, pp. 9-16, vol. 35, No. 1, NRC Research Press.

Usha Vyas et al., "Probiotics, Prebiotics, and Synbiotics: Gut and Beyond," Gastroenterology Research and Practice, Aug. 2012, vol. 2012, Hindawi Publishing Corporation.

Zhong Q. Wang et al., "Effects of dietary fibers on weight gain, carbohydrate metabolism, and gastric ghrelin gene expression in mice fed a high-fat diet," Metabolism Clinical and Experimental, Dec. 2007, pp. 1,635-1,642, vol. 56, No. 12, Elsevier.

Gary J. Grover et al., "Effects of the soluble fiber complex PolyGlycopleX® (PGX®) on glycemic control, insulin secretion, and GLP-1 levels in Zucker diabetic rats," Life Sciences, Feb. 2011, pp. 392-399, vol. 88, Elsevier.

Carpita N. and McCann M.,"The Cell Wall", in Biochemistry & Molecular Biology of Plants (2000), 1st Edition; Eds, Buchanan B. et al., Amer. Soc. Plant Physiol., Rockville, MD, pp. 52-108.

Cheetham Norman W.H., et al. "Structure of the principal nonstarch polysaccharide from the cotyledons of Lupinus angustifolius (cultivar Gungurru)", Carbohydrate Polymers (1993) 22: 37-47.

(56) References Cited

OTHER PUBLICATIONS

Kennedy, J.A. and Jones, G.P., Analysis of proanthocyanidin cleavage products following acid-catalysis in the presence of excess phloroglucinol, J. Agric. Food Chem. (2001) 49: 1740-1746.

Lavoine N., et al., "Microfibrillated cellulose—Its barrier properties and applications in cellulosic materials: A review", Carbohydrate Polymers (2012) 90: 735-764.

McCartney L., et al., "Temporal and spatial regulation of pectic (1-4)-B-D-galactan in cell walls of developing pea aotyledons: implications for mechanical properties", The Plant Journal (2000) 22(2): 105-113.

Mohnen D.,"Pectin structure and biosynthesis", Current Opinion in Plant Biology (2008) 11: 266-277.

Perrin R.M., et al."Xyloglucan Fucosyltransferase an Enzyme Involved in Plant Cell Wall Biosynthesis", Sciences, New Series (1999) 284(5422): 1976-1979.

Porter L.J., et al., "The conversion of procyanidins and prodelphinidins to cyanidin and delphinidin", Phytochemistry (1986) 25: 223-230.

Scheller H.V., et al., "Hemicelluloses", Annual Review of Plant Biology (2010) 61: 263-289.

Sinha Amit K., et al.,"Non-starch polysaccharides and their role in fish nutrition", Food Chemistry (2011) 127: 1409-1426.

Swain T. and Hillis W.E., "The phenolic constituents of Prunus Domestica", J. Sci. Food Agric. (1959) 10: 63-68.

Wikipedia, "Acid Strength".

Yang, Han, Excerpt from M.Sc. Thesis "Characterization of nutrient profiles from legume seeds", Jun. 2014, University of Alberta, Table 3.13 at p. 78 and accompanying description.

Craig Winston et al., "Phytochemicals: Health Protective Effects," Canadian Journal of Dietetic Practice and Research, Jun. 1999, pp. 78-84, vol. 60, No. 2.

Julie A. Ross et al., "Dietary Flavonoids: Bioavailability, Metabolic Effects, and Safety," Annual Review of Nutrition, Jul. 2002, pp. 19-34, vol. 22.

Laura Bravo, "Polyphenols: Chemistry, Dietary Sources, Metabolism, and Nutritional Significance," Nutritional Review, Nov. 1998, pp. 317-333, vol. 56, No. 11.

Augustin Scalbert et al., "Dietary Intake and Bioavailability of Polyphenols," The Journal of Nutrition, Aug. 2000, pp. 2073S-2085S, vol. 130, American Society for Nutritional Sciences.

Marja-Leena Ovaskainen et al., "Dietary Intake and Major Food Sources of Polyphenols in Finnish Adults," The Journal of Nutrition, Jan. 2008, pp. 562-566, vol. 138, No. 3, American Society for Nutrition.

Jara Perez-Jimenez et al, "Dietary intake of 337 polyphenols in French adults," The American Journal of Clinical Nutrition, Mar. 2011, pp. 1220-1228, vol. 93, No. 6.

Ying Wang et al., "Estimation of Daily Proanthocyanidin Intake and Major Food Sources in the U.S. Diet," The Journal of Nutrition, Jan. 26, 2011, pp. 447-452, vol. 141, No. 3, American Society for Nutrition.

Nicole M. Wedick et al., "Dietary flavonoid intakes and risk of type 2 diabetes in US men and women," The American Journal of Clinical Nutrition, Apr. 2012, pp. 925-933, vol. 95, No. 4, American Society for Nutrition.

Raul Zamora-Ros, et al., "Estimation of Dietary Sources and Flavonoid Intake in a Spanish Adult Population (EPIC-Spain)," Journal of the American Dietetic Association, Mar. 2010, pp. 390-398, vol. 110, No. 3, American Dietetic Association.

Z. Y. Chen et al., "Antioxidant activity of natural flavonoids is governed by number and location of their aromatic hydroxyl groups," Chemistry and Physics of Lipids, Mar. 29, 1996, pp. 157-163, vol. 79, issue 2, Elsevier.

Catherine A. Rice-Evans et al., "Structure-Antioxidant Activity Relationships of Flavonoids and Phenolic Acids," Free Radical Biology & Medicine, Mar. 1996, pp. 933-956, vol. 20, No. 7, Elsevier.

Joseph L. Evans et al., "Oxidative Stress and Stress-Activated Signaling Pathways: A Unifying Hypothesis of Type 2 Diabetes," Endocrine Reviews, Oct. 2002, pp. 599-622, vol. 23, No. 5, Endocrine Society.

Judith A. Bryans et al., "The Effect of Consuming Instant Black Tea on Postprandial Plasma Glucose and Insulin Concentrations in Healthy Humans," Journal of the American College of Nutrition, Oct. 2007, pp. 471-477, vol. 26, No. 5, American College of Nutrition.

Riitta Törrönen et al., "Postprandial glucose, insulin and glucagon-like peptide 1 responses to sucrose ingested with berries in healthy subjects," British Journal of Nutrition, May 2012, pp. 1,455-1,451, vol. 107, No. 10, The Authors.

S. Kirkham et al., "The potential of cinnamon to reduce blood glucose levels in patients with type 2 diabetes and insulin resistance," Diabetes, Obesity and Metabolism, Dec. 2009, pp. 1,100-1,113, vol. 11, No. 12, Blackwell Publishing Ltd.

Abir T. El-Alfy et al., "Protective effect of red grape seeds proanthocyanidins against induction of diabetes by alloxan in rats," Pharmacological Research, Sep. 2005, pp. 264-270, vol. 52, No. 3, Elsevier.

Myung-Jun Kim et al., "Protective Effects of Epicatechin Against the Toxic Effects of Streptozotocin on Rat Pancreatic Islets: In Vivo and in Vitro," Pancreas, Apr. 2003, pp. 292-299, vol. 26, No. 3, Lippincott Williams & Wilkins, Inc., Philadelphia.

Lídia Cedó et al, "Pancreatic islet proteome profile in Zucker fatty rats chronically treated with a grape seed procyanidin extract," Food Chemistry, Dec. 1, 2012, pp. 1,948-1,956, vol. 135, No. 3, Elsevier.

Ye Ding et al., "Grape seed proanthocyanidins ameliorate pancreatic beta-cell dysfunction and death in low-dose streptozotocin- and high-carbohydrate/high-fat diet-induced diabetic rats partially by regulating endoplasmic reticulum stress," Nutrition & Metabolism, Jul. 2013, 10:51, BioMed Central.

Min Zhu et al., "Effects of Long-Term Cranberry Supplementation on Endocrine Pancreas in Aging Rats," Journal of Gerontology: Biological Sciences, Nov. 2011, pp. 1,139-1,151, vol. 66, No. 11, Oxford University Press on Behalf of The Gerontological Society of America.

Sylvain Guyot., "Flavan-3-Ols and Proanthocyanidins," Handbook of Analysis of Active Compounds in Functional Foods, Jan. 18, 2012, pp. 317-348, CRC Press.

Angélique Stalmach et al., "Absorption, metabolism and excretion of Choladi green tea flavan-3-ols by humans," Molecular Nutrition & Food Research, May 2009, pp. S44-S53, 53, Wiley InterScience.

Angélique Stalmach et al., "Absorption, metabolism, and excretion of green tea flavan-3-ols in humans with an leostomy," Molecular Nutrition & Food Research, Mar. 2010, pp. 323-334, 54, Wiley InterScience.

Kathrin Kahle et al., "Studies on apple and blueberry fruit constituents: Do the polyphenols reach the colon after ingestion?," Molecular Nutrition & Food Research, Apr. 2006, pp. 418-423, 50, Wiley InterScience.

Gary Williamson et al., "Bioavailability and bioefficacy of polyphenols in humans. II. Review of 93 intervention studies," The American Journal of Clinical Nutrition, Jan. 2005, pp. 243S-255S, vol. 81, No. 1, American Society for Clinical Nutrition.

Barry Hallwell et al., "Health promotion by flavonoids, tocopherols, tocotrienols, and other phenols: direct or indirect effects? Antioxidant or not?," The American Journal of Clinical Nutrition, Jan. 2005, pp. 268S-276S, vol. 81, No. 1, American Society for Clinical Nutrition.

Kevin A. Whitlock et al., "Assessment of the mechanisms exerting glucose-lowering effects of dried peas in glucose-intolerant rats," British Journal of Nutrition, Aug. 2012, pp. S91-S102, vol. 108.

Lawrence J. Porter et al., "The Conversion of Procyanidins and Prodelphinidins to Cyanidin and Delphinidin," Phytochemistry, Dec. 23, 1985, pp. 223-230, vol. 25, issue 1, Pergamon Press Ltd, Great Britain.

Lihua Jin, "Flavonoids in Saskatoon Fruits, Blueberry Fruits, and Legume Seeds," University of Alberta, Oct. 2011, Edmonton, Alberta, Canada.

(56) References Cited

OTHER PUBLICATIONS

Sami Heikkinen et al., "Evaluation of Glucose Homeostasis," Current Protocols in Molecular Biology, Jan. 2007, pp. 29B.3-1-29B.3.22, John Wiley & Sons, Inc.

Catherine B. Chan et al., "Evidence for defective glucose sensing by islets of fa/fa obese Zucker rats," Canadian Journal of Physiology and Pharmacology, Jan. 1993, pp. 34-39, vol. 71, No. 1, Canada.

Catherine B. Chan et al., "Increased Uncoupling Protein-2 Levels in β-cells Are Associated With Impaired Glucose-Stimulated Insulin Secretion," Diabetes, Jun. 2001, pp. 1,302-1,310, vol. 50, No. 6.

Michael Zifkin et al., "Gene Expression and Metabolite Profiling of Developing Highbush Blueberry Fruit Indicates Transcriptional Regulation of Flavonoid Metabolism and Activation of Abscisic Acid Metabolism," Plant Physiology, Jan. 2012, pp. 200-224, vol. 158, No. 1, American Society for Plant Biologists.

Ram Weiss et al., "Basal α-Cell Up-Regulation in Obese Insulin-Resistant Adolescents," Journal of Endocrinology & Metabolism, Jan. 2011, pp. 91-97, vol. 96, No. 1, The Endocrine Society.

Lindsey N. Sutherland et al., "Time course of high-fat diet-induced reductions in adipose tissue mitochondrial proteins: potential mechanisms and the relationship to glucose intolerance," American Journal of Physiology—Endocrinology and Metabolism, Nov. 2008, pp. E1,076-E1,083, vol. 295, No. 5.

A. Brianne Thrush et al., "Conjugated linoleic acid increases skeletal muscle ceramide content and decreases insulin sensitivity in overweight, non-diabetic humans," Applied Physiology, Nutrition, and Metabolism, Jun. 2007, pp. 372-382, vol. 32, No. 3, NRC Canada.

Anwar Borai et al., "The biochemical assessment of insulin resistance," Annals of Clinical Biochemistry, Jul. 2007, pp. 324-342, vol. 44, The Association for Clinical Biochemistry.

Maria Monagas et al., "Insights into the metabolism and microbial biotransformation of dietary flavan-3-ols and the bioactivity of their metabolites," Food & Function, Dec. 2010, pp. 233-253, vol. 1, RSC Publishing.

Fulgencio Saura-Calixto et al., "Proanthocyanidin metabolites associated with dietary fibre from in vitro colonic fermentation and proanthocyanidin metabolites in human plasma," Molecular Nutrition & Food Research, Jul. 2010, pp. 939-946, vol. 54, No. 7, Wiley InterScience.

María Luisa Mateos-Martín et al., "Non-extractable proanthocyanidins from grapes are a source of bioavailable (epi)catechin and derived metabolites in rats," British Journal of Nutrition, Jul. 2012, pp. 290-297, vol. 108, No. 2, The Authors.

Richard W. Hemingway et al., "Kinetics of Acid-Catalyzed Cleavage of Procyanidins," Journal of Wood Chemistry and Technology, 1983, pp. 421-435, vol. 3, No. 4.

Catherine Tsang et al., "The absorption, metabolism and excretion of flavan-3-ols and procyanidins following the ingestion of a grape seed extract by rats," British Journal of Nutrition, Aug. 2005, pp. 170-181, vol. 94, No. 2, The Authors.

Toshihiko Shoji et al., "Apple Procyanidin Oligomers Absorption in Rats after Oral Administration: Analysis of Procyanidins in Plasma Using the Porter Method and High-Performance Liquid Chromatography/Tandem Mass Spectrometry," Journal of Agricultural and Food Chemistry, Feb. 2006, pp. 884-892, vol. 54, No. 3, American Chemical Society.

Stavroula Stoupi et al., "In vivo bioavailability, absorption, excretion, and pharmacokinetics of [14C]procyanidin B2 in male rats," Drug Metabolism and Disposition, Feb. 2010, pp. 287-291, vol. 38, No. 2, American Society for Pharmacology and Experimental Therapeutics.

Alexandra H. Smith et al., "Bacterial Mechanisms to Overcome Inhibitory Effects of Dietary Tannins," Microbial Ecology, Aug. 2005, pp. 197-205, vol. 50, issue 2, Springer Science+Business Media, Inc.

Alexandra H. Smith et al., "Effect of Condensed Tannins on Bacterial Diversity and Metabolic Activity in the Rat Gastrointestinal Tract," Applied and Environmental Microbiology, Feb. 2004, pp. 1,104-1,115, vol. 70, No. 2, American Society for Microbiology.

Jun Yamakoshi et al., "Effect of Proanthocyanidin-Rich Extract from Grape Seeds on Human Fecal Flora and Fecal Odor," Microbial Ecology in Health and Disease, Jan. 2001, pp. 25-31, vol. 13, Taylor & Francis.

Marlon E. Cerf et al., "High-Fat Programming of Hyperglycemia, Hyperinsulinemia, Insulin Resistance, Hyperleptinemia, and Altered Islet Architecture in 3-Month-OldWistar Rats," ISRN Endocrinology, Sep. 2012, International Scholarly Research Network.

Bo Ahré et al., "Islet Perturbations in Rats Fed a High-Fat Diet," Pancreas, Jan. 1999, pp. 75-83, vol. 18, No. 1, Lippincott Williams & Wilkins, Philadelphia.

Bolleddula Jayaprakasam et al., "Insulin Secretion by Bioactive Anthocyanins and Anthocyanidins Present in Fruits," Journal of Agricultural and Food Chemistry, Jan. 2005, pp. 28-31, vol. 53, No. 1, American Chemical Society.

Hashemi et al., "Cooking enhances beneficial effects of pea seed coat consumption on glucose tolerance, incretin, and pancreatic hormones in high-fat-diet-fed rats," Appl. Physiol. Nutr. Metab., 2015, pp. 323-333, 40, Edmonton, Canada.

Yang et al., "Hydrolysis enhances bioavailability of proanthocyanidin-derived metabolites and improves β-cell function in glucose intolerant rats," Journal of Nutritional Biochemistry, 2015, pp. 850-859, vol. 26.

* cited by examiner

FIGURE 2
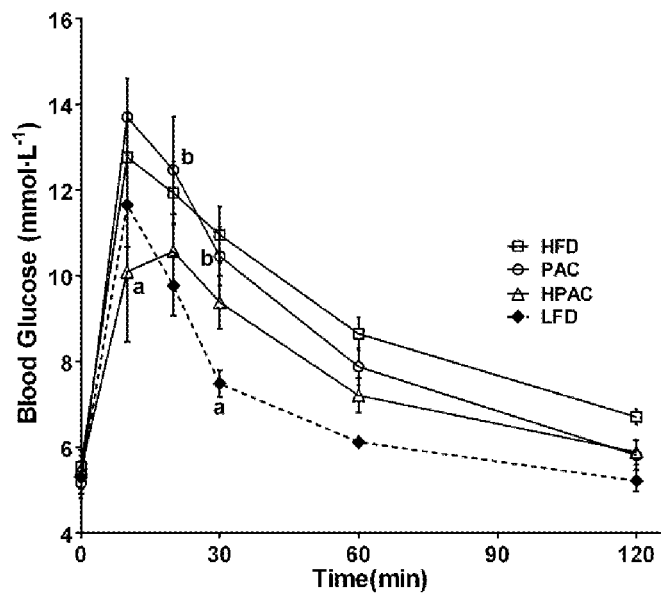
A
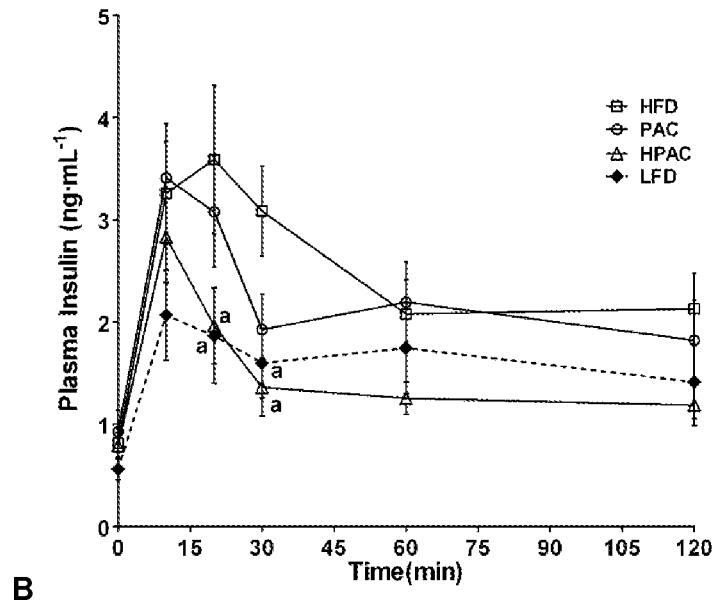
B

FIGURE 2
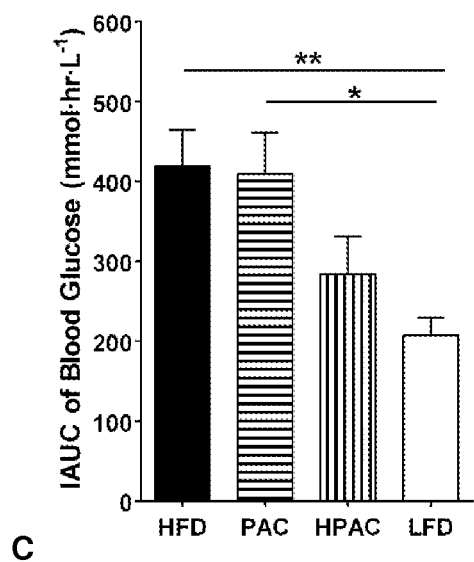
C
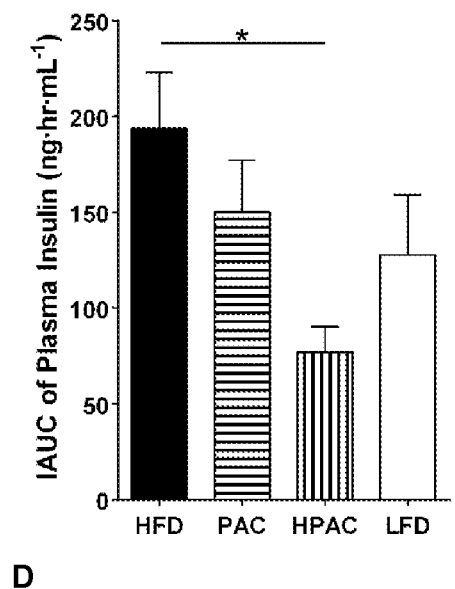
D

FIGURE 3
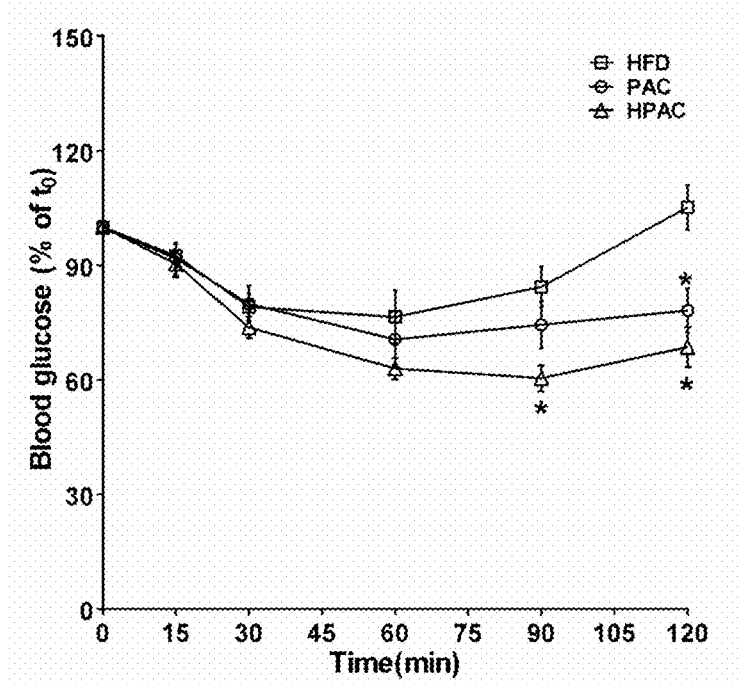
A
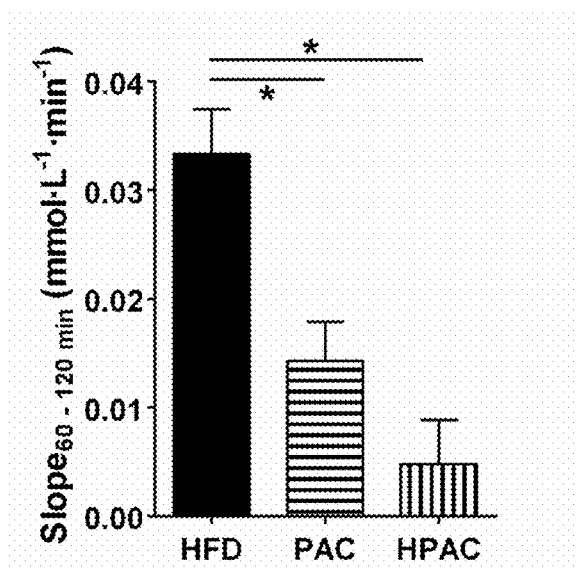
B

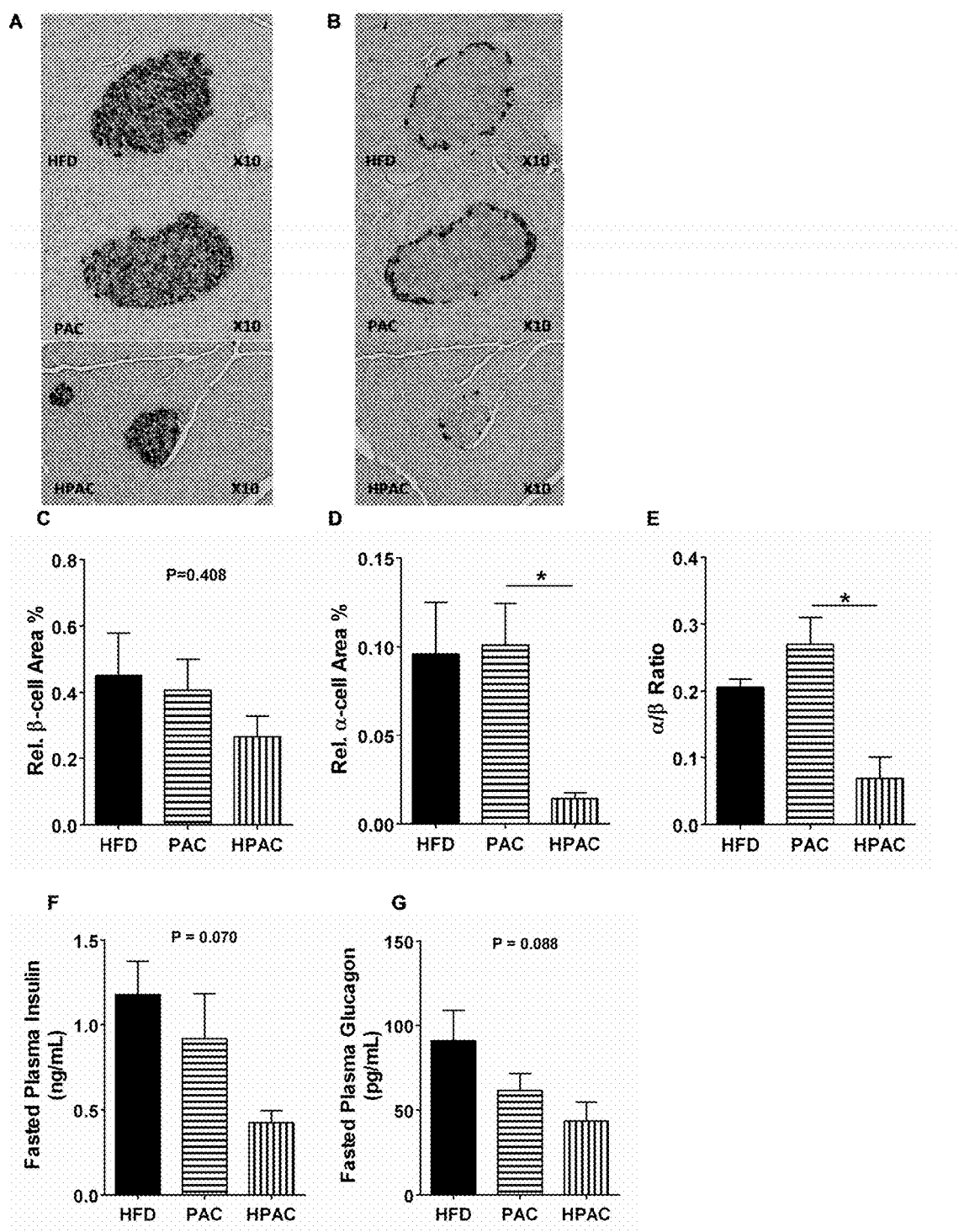
Figure 4. Effects of diet on pancreatic morphology, fasted insulin and glucagon

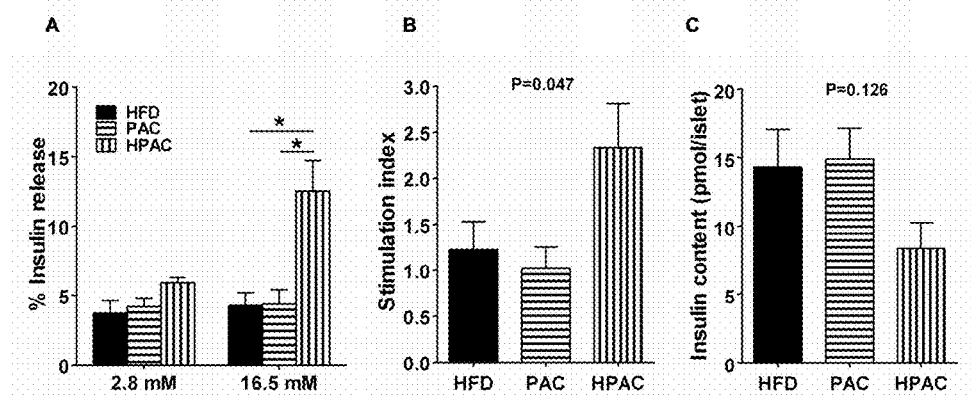
Figure 5. Effects of diet on glucose-stimulated insulin secretion from isolated islets

FIGURE 6A
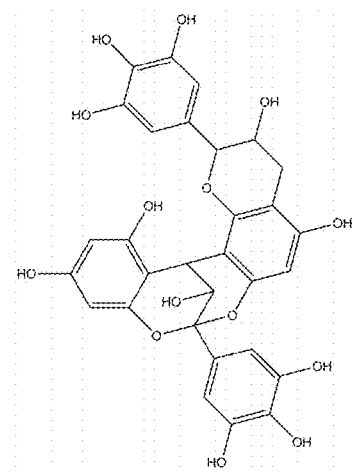
Prodelphinidin A1
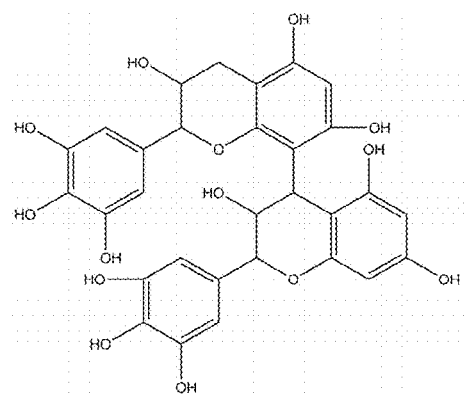
Prodelphinidin B
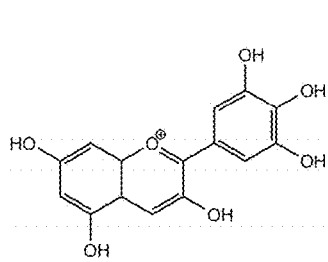
Delphinidin
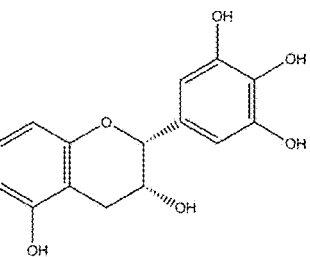
(-)-Epigallocatechin
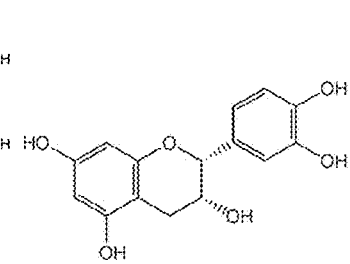
(-)-Epicatechin
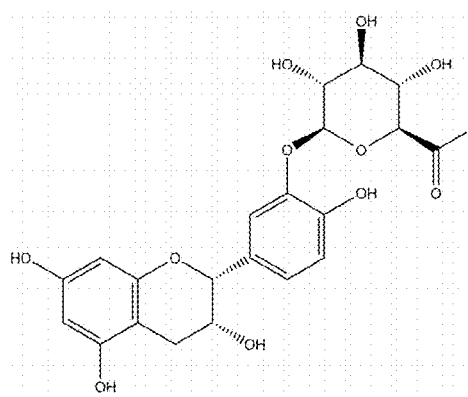
Epicatechin 3'-O-glucuronide
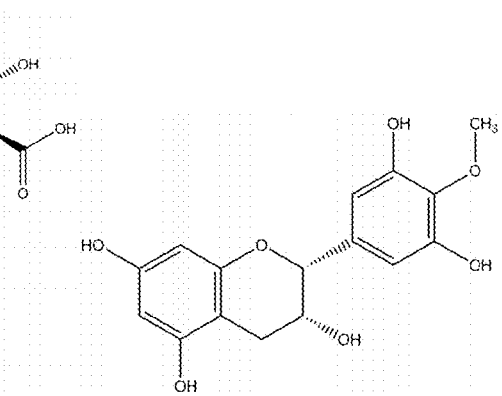
4'-O-Methyl-epigallocatechin

PEA (*PISUM SATIVUM* L.) SEED COATS AND SEED COAT FRACTIONS

CROSS-REFERENCE TO RELATED APPLICATION

This application claims priority to U.S. Provisional Application No. 62/041,277, filed Aug. 25, 2014.

SEQUENCE LISTING

The instant application contains a Sequence Listing which has been submitted electronically in ASCII format and is hereby incorporated by reference in its entirety. Said ASCII copy, created on Nov. 2, 2015, is named 5717-001U_SL.txt and is 6,701 bytes in size.

FIELD

The present disclosure relates to pulse grains and methods and compositions for improving health and/or beneficial effects in a human and/or animal diet.

INTRODUCTION

Plant-based foods provide a significant amount of phytochemicals in our diet. Phytochemicals are non-nutrient compounds that have biological activity in the body [1]. Among them, flavonoids have been extensively studied because they exhibit a variety of physiological effects [2]. A subgroup of flavonoids, proanthocyanidins (PAC, or condensed tannins) are the oligomers and polymers of flavan-3-ols [3]. They exist in a variety of foods such as peas, beans, nuts, spices, fruits, wine and tea, and contribute the most to total flavonoid intake in the diet [4]. The estimated average dietary intake of PAC varies from 95-227 mg/d in different populations [5-9].

The availability of the phenolic hydrogens as hydrogen-donating radical scavengers and singlet oxygen quenchers predicts PAC antioxidant activity [10,11]. PAC as well as their monomeric flavan-3-ol subunits and hydrolysis-derived anthocyanin products can scavenge free radicals and reactive oxygen species (ROS) such as hydroxyl and peroxy radicals [10,11], which play a significant role in inducing oxidative stress [12], hence, research has been focused on their effects on alleviating oxidative stress.

Evidence is emerging to support consumption of PAC-rich foods to improve glycemic control. Black tea [13] and berries [14] reduced postprandial glycemia and moderately increased plasma glucagon-like peptide-1 in healthy subjects. Improvement in insulin sensitivity and lowered fasting blood glucose were observed in randomized clinical trials that evaluated the therapeutic potential of cinnamon amongst diabetic and insulin-resistant patients [15].

Animal studies suggest that PAC may exert effects on the endocrine pancreas. Grape seed PAC extracts alleviated oxidative stress in alloxan-induced diabetic rats by increasing pancreatic glutathione concentrations and reducing of lipid peroxidation [16]. Green tea epicatechin preserved pancreatic islet morphology and function against streptozotocin (STZ) toxicity both in vivo and in vitro [17]. Grape seed PAC extracts favorably modulated proteins involved in insulin synthesis and secretion [18]. PAC also prevented β-cell loss caused by aging and apoptosis [18-20].

Thus, findings from studies both in vivo and in vitro indicate PAC's physiological role in modulating glucose homeostasis in the body, potentially by acting on cell signalling pathways to improve pancreatic β-cell function. However, plant-derived PAC are polymeric structures with a wide degree of polymerization (DP) range; therefore, the absorption and bioavailability of native PAC is limited [21]. Many in vitro PAC mechanistic studies tested concentrations not relevant to dietary intake and absorption, whereas the amount of PAC absorbed into the body was not quantified in most in vivo studies. Other obstacles included lack of knowledge of the metabolism of PAC in humans, lack of biomarkers specific for PAC intake and insufficiently sensitive analytical methods for PAC and metabolites. The existing bioavailability studies only detect trace amounts of PAC with DP<2, usually pmol/L or nmol/L, in the urine and plasma [22-25]. This concentration range of PAC is not likely to have antioxidant actions in the body [26].

SUMMARY

Disclosed is a method for improving health and/or other beneficial effects in a subject, comprising administering pea seed coat fractions to said subject. In some embodiments, said subject is a human or animal. In some embodiments, said health and/or beneficial effect is selected from retained PAC bioavailability, retained PAC bioactivity, improved insulin sensitivity, reduced glycemia, increased satiety, improved glucose tolerance, improved glucose control, improved glucose homeostasis, beneficial effects on pancreatic islet composition and insulin secretion. In some embodiments, said health and/or beneficial effect is selected from PAC-derived products that have increased bioavailability, improved insulin sensitivity, reduced glycemia, increased satiety, improved glucose tolerance, improved glucose control, improved glucose homeostasis, beneficial effects on pancreatic islet composition and insulin secretion.

Disclosed is a composition comprising pea seed coat fractions. In some embodiments, said composition is selected from a food, animal feed, flour, fibre, and ingredient.

Disclosed is a method for improving health and/or other beneficial effects in a subject, comprising administering cooked pea seed coat fractions to said subject.

Disclosed is a method for improving health and/or other beneficial effects in a subject, comprising administering pea seed coat fractions processed by cooking followed by freeze-drying to said subject.

Disclosed is method for increasing the bioavailability of proanthocyanidins (PAC), comprising hydrolyzing pea seed coat-derived PACs.

BRIEF DESCRIPTION OF THE DRAWINGS

FIG. 3: Blood glucose responses after insulin challenge in rats fed PAC or HPAC. Insulin tolerance tests were performed before the day of tissue collection. After 4 h fasting, blood glucose levels was measured at 0, 15, 30, 60, 90, 120 min after intraperitoneal administration of 5 U/kg body weight insulin. Changes in blood glucose (A) are expressed as percent of 4 h-fasted glucose and (B) slopes for 60-120 min were calculated as a direct measurement of glucose recovery rate (Borai et al., 2007). N=8 for all groups. *P<0.05, Bonferroni's multiple comparison.

FIG. 4: Effects of different diets on pancreatic morphology, fasted insulin and glucagon in rats fed PAC or HPAC. Immunohistochemical staining of insulin and glucagon (n=5 for all groups) was shown in panel (A) and (B), respectively. The percentages of insulin (C)- or glucagon (D)-positive area versus the total pancreas areas were calculated as estimates of pancreatic β- or α-cell mass. The ratio of α- to β-cell area (E) was calculated to reflect cell composition of pancreatic islets. Fasted plasma insulin (F, n=8 for all groups) and glucagon (G, n=6 for all groups) were also measured. *P<0.05, Bonferroni's multiple comparison.

FIG. 5: Effects of different diets on glucose-stimulated insulin secretion from isolated islets of rats fed PAC or HPAC. Isolated islets were cultured in fresh medium plus 2.8 and 16.5 mmol/L glucose for 2 h. Insulin secretion (A) is presented as percent of total content. Insulin content (B) and insulin stimulation index (C) were calculated as described above. N=5 for all groups. *P<0.05, Bonferroni's multiple comparison.

FIG. 6A: Structures of pea seed coat PAC dimers, the acid hydrolyzed PAC-derived compound delphinidin, PAC subunit flavan-3-ols epigallocatechin and epicatechin, and serum-derived metabolites.

DETAILED DESCRIPTION

Figure 1:
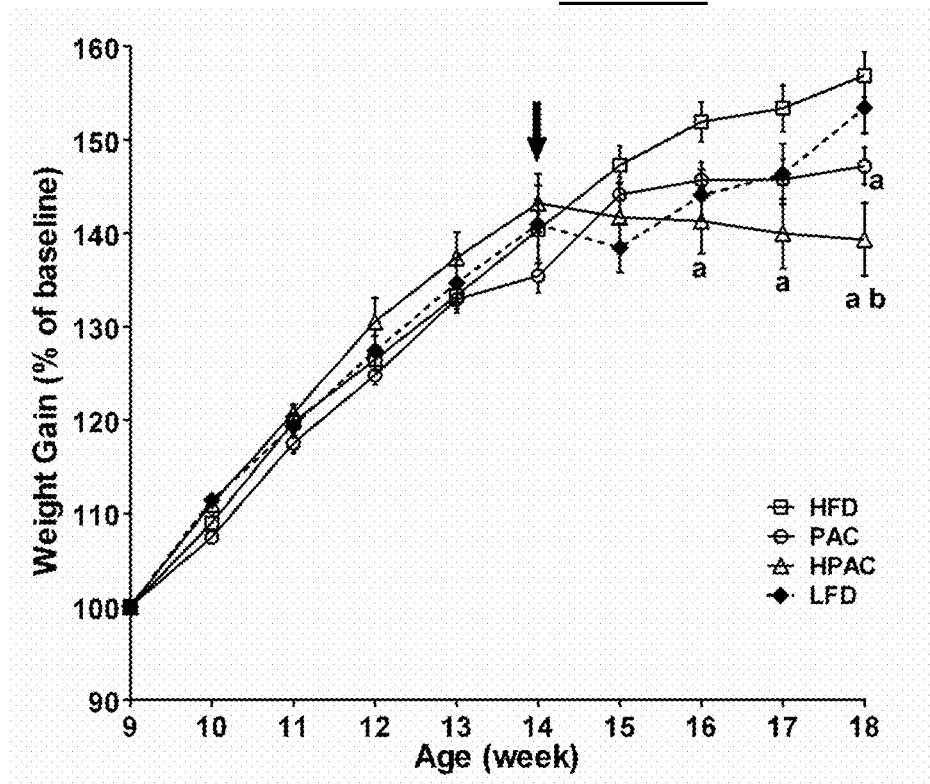
FIG. 1: Effects of diet on body weight change during the PAC/HPAC feeding trial. Male Sprague Dawley rats were fed 20% w/w high fat diet (HFD) for 6 weeks, then were randomly assigned [arrow] to HFD (n=23), 0.8% w/w proanthocyanidin+HFD (PAC, n=22), or 0.8% w/w hydrolyzed proanthocyanidin+HFD (HPAC, n=19) and maintained for 4 weeks. Additional rats were fed 6% w/w low fat diet (LFD, n=20) for 10 weeks as a normal control. Body weight was recorded weekly. Data are presented as percentage of the baseline weights. $^{a}P<0.05$ compared with HFD, $^{b}P<0.05$ compared with LFD, Bonferroni's multiple comparison.

Pulse grains, including dried peas, provide rich sources of fibre with low glycemic indices. Their unique nutritional profile has led to many studies investigating different varieties of pulses in terms of their health benefits. Sievenpiper et al. (2009) found that consumption of non-oil-seed pulses was associated with enhanced long-term glycemic control. Consumption of dried peas has specifically been linked with enhanced glycemic control in several human intervention studies. Type 2 diabetic patients consuming a mixed meal containing whole dried peas had a delayed increase in postprandial plasma glucose and insulin concentration compared with controls eating potato-based meals (Schafer et al., 2003) and whole pea flour muffins ameliorated insulin sensitivity in overweight subjects compared with wheat flour muffins (Marinangeli & Jones, 2011).

Most studies identifying beneficial effects of pulses on glycemia have used the whole grain (Sievenpiper et al., 2009) but recent studies consider pulse fractions. In an animal study, for example, feeding hamsters a hypercholesterolemic diet with partial substitution of cornstarch with pea hull flour resulted in significant decreases in circulating glucose and insulin levels (Marinangeli et al., 2011). Lunde et al. (2011) also showed that consumption of pea fibre-enriched breads resulted in improved post-prandial glucose tolerance and increased satiety in human subjects with a high risk of developing type 2 diabetes.

While these studies suggest seed coat fractions contribute beneficial effects, the data remains inconclusive because of inconsistent and variable preparations of the fractions. In humans, for example, fraction processing by gastric enzymes may reduce beneficial effects. There are also industrial processes that may reduce beneficial effects (e.g., spray drying), although this has not been systematically evaluated.

As described below, the present inventors developed methodology for preparing pea seed coat fractions conferring improved health and/or other beneficial effects, and such fractions may be used in a human and/or animal diet. In so doing, the present inventors developed methodology for preparing seed coat fractions with retained bioactivity. That is, and in one embodiment, the present inventors realized that seed coat PAC can be hydrolyzed to reduce the polymeric nature of PAC. In another embodiment, the present inventors determined that pea seed coat fractions can be ground, cooked, and then freeze dried, and that such pea seed coat fractions confer beneficial effects on glucose tolerance, incretin concentrations, and pancreatic hormones.

For example, and as described below, the seed coats of the pea (*Pisum sativum*) cultivar 'Solido', a marrowfat-type field pea with brown seed coats containing primarily prodelphinidin-type PAC with B-type PAC linkages and a mean DP of 5, were acid hydrolyzed. In so doing, the bioavailability and effects of both PAC and hydrolyzed PAC (HPAC) PSC fractions were demonstrated by evaluating glucose homeostasis in rats. The hydrolyzed PAC (HPAC) fraction has enhanced bioavailability and therefore better effects on glycemic control.

Because the present inventors discovered that seed coat PAC can be acid-hydrolyzed to reduce the polymeric nature of PAC, and that the PAC (HPAC) fraction has enhanced bioavailability, such pea seed coat fractions can be used as or in a variety of products including but not limited to ingredients, food products, and animal feed.

In another embodiment, the present inventors determined that cooked pea seed coats confer health benefits, such as, for example, improved glucose tolerance.

Technical terminology in this description conforms to common usage in plant physiology, molecular biology, biochemistry, agriculture, and the like.

As used herein, seed coat refers to the seed hull and comprises mostly soluble and insoluble fibre. A seed coat fraction refers to the portion of a seed comprising the seed coat. The terms seed coat fraction and fraction are used interchangably, as they both refer to the portion of the seed comprising the seed coat.

Pulse grains, also called pulses or grain legumes, belonging to the family Leguminosae (alternatively Fabaceae) and are grown primarily for their edible grains or seeds. Pulses, such as dried peas, provide rich sources of fibre with low glycemic indices. These seeds are harvested mature and marketed dry, and used as food or feed.

Proanthocyanidins (PAC, or condensed tannins) are the oligomers and polymers of flavan-3-ols. They exist in a variety of foods such as peas, beans, nuts, spices, fruits, wine and tea, and contribute the most to total flavonoid intake in the diet. PACs generally accumulate in the seed coat of some legume seeds, as evidenced by their browinsh coloration due to oxidation by polyphenol oxidase.

Bioavailability or PAC bioavailability refers to the degree and rate at which a substance (as a drug, or PAC) is absorbed into a living system or made available at the site of physiological activity. PAC bioavailability is profoundly affected by its degree of polymerization (DP). For example, PAC with DP<3 are believed to be absorbed from the small intestine, whereas PAC with DP>3 reach the colon, where they are subjected to microbial metabolism, and the degraded products either get absorbed or excreted in the feces. Furthermore, in fibre-rich plant samples such as those used herein, non-extractable PAC is found associated with fibre, which makes it even less bioavailable. Acid hydrolysis of PAC can break the interflavan bonds, which increases bioavailability. Hydrolysis of PAC (HPAC) significantly increased its bioavailability reflected by detection of PAC-derived metabolites only in the serum of HPAC-fed rats.

Improved health-beneficial effects refers to the ability of the instant methodology and/or compositions to confer health and/or other beneficial effects in a human and/or animal. For example, and in no way limiting, such improved heath and/or beneficial effects include any of retained PAC and PAC component bioavailability, retained PAC and PAC component bioactivity, improved insulin sensitivity, reduced glycemia, increased satiety, improved glucose tolerance, improved glucose control, improved glucose homeostasis, beneficial effects on pancreatic islet composition and insulin secretion, improved incretin secretion, lower body weight, lower body fat content, and improved serum lipids.

A. Pulses

Pulse grains, also called pulses or grain legumes, belonging to the family Leguminosae (alternatively Fabaceae) and are grown primarily for their edible grains or seeds. Pulses, such as dried peas, provide rich sources of fibre with low glycemic indices. They are also good sources of protein. These seeds are harvested mature and marketed dry, and used as food or feed.

Illustrative pulses include but are not limited to adzuki beans (e.g., azuki, Adanka, danka), broad beans (e.g., faba bean, fava bean, bell bean), vetch, common beans (e.g., field bean, dry bean, kidney bean, navy), chick pea (e.g., bengal gram, garbanzo bean, yellow gram), cowpea (e.g., asparagus bean, black eyed pea, frijole), guar bean (e.g., cluster bean, gawaar), hycainth bean (e.g., bonavist, bataw, lablab), lentil (e.g., green lentil, yellow lentil, mungbean), lima bean (e.g., butter bean), lupin (e.g., lupine, sweet lupin), mung bean (e.g., black dahl, urd, chop suey), pea (e.g., dry pea, field pea, Chinese pea), peanut (e.g., ground nut, earth nut, Virginia peanut), pigeon pea (e.g., kadios), soybean (e.g., soya, edamame), and tepary bean (e.g., tepari bean).

The pea seed (*Pisum sativum* L.) consists of an embryo (cotyledons and an embryo axis), which is enclosed in a seed coat (hull). The nutrient components of the embryo are mostly starch and protein, while the seed coats are largely soluble and insoluble fibre (Whitlock et al., 2012; Guillon & Champ, 2002; Duenas et al., 2004). Many studies have shown that dietary fibre has positive effects on postprandial glucose control (reviewed by Babio et al., 2010). It was concluded that a high intake of soluble dietary fibre (SDF) is associated with reduced postprandial glucose levels. However, deeper insights into the mechanisms by which different sources of fibre affect glucose metabolism are yet to be elucidated. It is known that dietary fibre is fermented by colon microflora, producing short-chain fatty acids (SCFA) like acetate, propionate, and butyrate (Jenkins et al., 2000). Increased accumulation of SCFA has been linked with decreased production of glucose in the liver (Galisteo et al., 2008). Soluble fibre also dissolves in water to form a viscous slow-moving solution that results in slowed gastric emptying; however, the effect of this increased transit time on digestion and absorption is controversial (Haub & Lattimer, 2010).

Applicants previously showed that insulin-resistant rats fed a raw pea seed coat-supplemented diet had better glucose homeostasis compared to embryo-supplemented diet fed rats, suggesting that the beneficial effects are associated with the seed coat fraction (Whitlock et al., 2012). One limitation of that study was that raw pea seed coats incorporated into the diet were not suitable for human consumption. Some studies have suggested that processing reduces the effectiveness of pulses in improving glycemia (Jenkins et al., 1982). Therefore, this study was undertaken to examine the effects of grinding and cooking followed by freeze-drying on the ability of pea seed coat fractions to improve glucose control and to identify potential physiological mechanisms. Supplementing diets with pea seed coat fractions may ameliorate glucose tolerance by modulating glucose handling by the gut and reducing high fat diet-induced stress on pancreatic islets. Further, cooking should not destroy the beneficial effects of pea seed coat fibre consumption.

B. Bioavailability and Effects on Glucose Homeostasis of PAC and HPAC Pea Seed Coat Fractions A main objective of this study was to evaluate the bioavailability and compare effects on glucose homeostasis of PAC and HPAC pea seed coat fractions. As described below and in the Examples, the present inventors discovered that PAC's biological functions are clearly determined by its bioavailability in vivo. PAC-related metabolites were only detected in serum of HPAC-fed rats, and this was associated with a more pronounced beneficial effect of HPAC on body weight gain, glucose tolerance and pancreatic β-cell function.

PAC bioavailability is profoundly affected by its degree of polymerization (DP). PAC with DP<3 are believed to be absorbed from the small intestine, whereas PAC with DP>3 reach the colon, where they are subjected to microbial metabolism, and the degraded products either get absorbed or excreted in the feces [38]. The absorbed compounds are extensively metabolised in the enterocytes and liver by phase II enzymes into conjugated derivatives, such as glucuronides, sulfate conjugates and methyl derivatives; these either persist in the circulation or are rapidly eliminated in urine [38]. Furthermore, in fibre-rich plant samples such are were used in this diet study, non-extractable PAC is found associated with fibre, which makes it even less bioavailable [39,40]. Acid hydrolysis of PAC can break the interflavan bonds [21,41]. It is also possible that acid hydrolysis can break the association of non-extractable PAC with fibre, although this was not explicitly evaluated.

As shown below, hydrolysis of PAC (HPAC) significantly increased its bioavailability reflected by detection of PAC-derived metabolites only in the serum of HPAC-fed rats. This is in accordance with the findings of previous bioavailability studies showing that the small molecular weight PAC (monomers and dimers) can be absorbed and metabolized [42-44]. Because PAC has growth-inhibitory effects on bacteria [45] and some "tannin-resistant" species are candidates for PAC metabolism [46,47], it is also possible that hydrolysis reduced PAC growth-inhibitory effects on gut microbes and therefore more microbial metabolites were produced and absorbed in HPAC-treated rats.

Prolonged HFD feeding is well known to induce insulin resistance and glucose intolerance in rats. Hyperplasia of β-cells develops to adapt to changes in metabolic status and maintain glucose homeostasis [48,49]. Incorporating HPAC to into HFD led to correction of glucose intolerance: both glucose excursion and insulin secretion of HPAC was similar to LFD in the IPGTT, while there was prolonged suppression of blood glucose in the ITT. Meanwhile, consistent with the reduced insulin response during IPGTT, pancreatic β-cell areas in HPAC was ~50% less than HFD (p=0.4). Therefore, HPAC was able to reduce the demand for insulin compensation caused by HFD.

Insulin secretion from the islets in response to high glucose (16 mM) stimulation was significantly enhanced in HPAC vs HFD. There may be two explanations for this improvement. Firstly, PAC may act as an insulin secretagogue. INS-1 cells pre-cultured with PAC-rich cranberry powder had increased basal and stimulated insulin secretion [20]. Jayaprakasam et al. [50] tested the effects of a series of anthocyanins from fruits on insulin secretion in vitro. They found delphinidin-3-glucoside was the most effective stimulant of GSIS. However, neither the forms nor the concentrations (cranberry powder: 0.25 and 0.5 mg/mL; anthocyanins: 50 µg/mL) of compounds used in their studies is likely to exist in physiological post-absorptive conditions. According to the present inventors' findings, PAC-derived compounds (including 4'-O-methyl-epigallocatechin (main metabolite) and epicatechin-3'-O-glucuronide) were identified in the serum of HPAC-fed rats only (Table 2). These compounds existing in nanomolar quantities in the circulation are likely candidates for the bioactive substances that regulate GSIS.

On the other hand, improved GSIS may be the indirect result of the improved insulin sensitivity in HPAC. The demand for insulin secretion in HPAC was lower than the HFD group, thus creating less stressful condition for β-cells leading to better pancreatic function. These possibilities will be tested in future in vitro assays designed to assess direct effects on β-cells or insulin-sensitive tissues.

Additionally, the present disclosure shows a striking reduction in α-cell area and α/β cell ratio in HPAC pancreas, while plasma glucagon concentrations were reduced by 50% in HPAC vs HFD (p<0.07). In type 2 diabetes, increased relative or absolute mass of α-cells has been proposed to play a role in the pathology in addition to β-cell loss and dysfunction [51,52]. Elevated plasma glucagon concentration relative to insulin is believed to cause hyperglycemia and dysregulated glucose metabolism [53,54]. Therefore, in addition to improved insulin sensitivity, the glucagon secreting capacity may also contribute to the better glycemic control in HPAC group, as exemplified by the slower glucose rebound after ITT. The 60-120 minute phase of the ITT reflects the counter-regulatory response, the strength of which is dictated, in part, by the suppressive effect of insulin versus the positive effect of glucagon on hepatic glucose production [55].

Another interesting finding is that HPAC group exerted a favorable effect on body composition without altered energy intake. Dietary polyphenols such as catechins have the potential to modulate neuropeptides involved in energy expenditure [56,57] and catechins and PAC metabolites are able to cross the blood-brain barrier [58-60]. Wang et al. reported that the metabolite concentrations were about 300 pmol/gram of brain tissue after 10-day treatment, and basal synaptic transmission was significantly improved when using a biosynthetic brain-targeted PAC metabolite at a physiologically relevant concentration (300 nM) [60]. Another mechanism may relate to changes in fatty acid oxidation and metabolism.

In summary, and in one embodiment, the present inventors determined that acid hydrolysis improved the limited bioavailability of PAC fractions, resulting in the detection of PAC-related metabolites in HPAC serum. This was associated with enhanced improvement in glucose handling in glucose intolerant rats. Beneficial effects on pancreatic islet composition and insulin secretion were also elicited by HPAC treatment.

C. Cooking Enhances Beneficial Effects of Pea Seed Consumption on Glucose Tolerance, Incretin and Pancreatic Homeostasis of Pea Seed Coat Fractions The pea seed (*Pisum sativum* L.) consists of an embryo (cotyledons and an embryo axis), which is enclosed in a seed coat (hull). The nutrient components of the embryo are mostly starch and protein, while the seed coats are largely soluble and insoluble fibre (Whitlock et al., 2012; Guillon & Champ, 2002; Duenas et al., 2004). Many studies have shown that dietary fibre has positive effects on postprandial glucose control (reviewed by Babio et al., 2010). It was concluded that a high intake of soluble dietary fibre (SDF) is associated with reduced postprandial glucose levels. However, deeper insights into the mechanisms by which different sources of fibre affect glucose metabolism are yet to be elucidated. It is known that dietary fibre is fermented by colon microflora, producing short-chain fatty acids (SCFA) like acetate, propionate, and butyrate (Jenkins et al., 2000). Increased accumulation of SCFA has been linked with decreased production of glucose in the liver (Galisteo et al., 2008). Soluble fibre also dissolves in water to form a viscous slow-moving solution that results in slowed gastric emptying; however, the effect of this increased transit time on digestion and absorption is controversial (Haub & Lattimer, 2010).

Applicants previously showed that insulin-resistant rats fed a raw pea seed coat-supplemented diet had better glucose homeostasis compared to embryo-supplemented diet fed rats, suggesting that the beneficial effects are associated with the seed coat fraction (Whitlock et al., 2012). One limitation of that study was that raw pea seed coats incorporated into the diet were not suitable for human consumption. Some studies have suggested that processing reduces the effectiveness of pulses in improving glycemia (Jenkins et al., 1982).

Herein, the present inventors examined the effects of grinding and cooking followed by freeze-drying on the ability of pea seed coat fractions to improve glucose control and to identify potential physiological mechanisms. In so doing, they discovered that supplementing diets with pea seed coat fractions may ameliorate glucose tolerance by modulating glucose handling by the gut and reducing high fat diet-induced stress on pancreatic islets. The beneficial effects of pea seed coat fibre consumption is not lost following cooking.

D. Products

The instant methodology and materials may be used for creating a product conferring novel health and/or beneficial effects in a human and/or animal diet. In no way limiting, illustrative products include foods, flours, fibres, pet foods, compositions, and other ingredients, any of which may comprise pea seed coat fractions.

Specific Examples are provided below to demonstrate preparation of illustrative embodiments, including material and methodology. The Examples are illustrative and non-limiting.

Disclosed below are findings from two feeding trials examining different aspects of pea seed coat preparation, namely, hydrolysis of PAC versus cooking followed by freeze-drying of seed coats not containing PAC.

As evidenced below, Section I (Examples 1-14) demonstrates that hydrolysis enhances bioavailability and improves beneficial effects, and Section II (Examples 15-30) demonstrates that cooking and stabilization of cooking-induced changes by freeze-dying enhances the beneficial effects of PSC consumption.

I. Hydrolysis Enhances Bioavailability of PAC

Example 1: Preparation of Pea Seed Coat Diet

Seed coats of pea (*Pisum sativum* L.) cultivar 'Solido' were obtained from Mountain Meadows Food Processing Ltd. (Legal, Alberta). The smaller seed fragments were removed from the bulk PSC sample using a 1.0 mm screen (Canadian Standard sieve series #18, W.S. Tyler Co. of Canada, St. Catherines, ON). The cleaned PSC were then ground into a powder using a standard electric coffee grinder for rat feeding studies. A portion of the ground samples were used unprocessed (PAC fraction) and a portion was subjected to acid hydrolysis (HPAC fraction).

For acid hydrolysis, a 2N HCl solution (1 L total volume consisting of 170 mL food grade HCl, 330 mL deionized water and 500 mL ethanol) was added to ~200 g of ground 'Solido' PSC, making a slurry. Acid hydrolysis was performed by placing the PSC slurry into a 100° C. water bath for 1 h (from the time the slurry came to a boil). After 1 h of slurry boiling, the mixture was cooled down to approximately room temperature using an ice bath. Saturated NaOH solution (approximately 78 g NaOH) was slowly added into the slurry to neutralize the excess HCl. After neutralization, the PSC slurry was lyophilized using a freeze dryer. PAC and HPAC fractions were added to a high fat diet (HFD) (Table 1) such that the final concentration of both was 0.8% (w/w).

TABLE 1

Experimental Diets Formula (g)

| Ingredient | HFD | PAC | HPAC | LFD |
|---|---|---|---|---|
| Stearine | 99.5 | 99.5 | 99.5 | 29.85 |
| Flaxseed oil | 6 | 6 | 6 | 1.8 |
| Sunflower oil | 94.5 | 94.5 | 94.5 | 28.35 |
| Casein | 270 | 254 | 254 | 270 |
| L-Methionine | 2.5 | 2.5 | 2.5 | 2.5 |
| Dextrose | 189 | 189 | 189 | 255 |
| Corn Starch | 169 | 169 | 169 | 245 |
| Cellulose | 100 | 0 | 0 | 100 |
| 'Solido' seed coat (raw or hydrolyzed) | 0 | 193 | 193 | 0 |
| Mineral Mix | 51 | 51 | 51 | 51 |
| Vitamin Mix | 10 | 10 | 10 | 7.6 |
| Inositol | 6.3 | 6.3 | 6.3 | 6.3 |
| Choline Chloride | 2.8 | 2.8 | 2.8 | 2.8 |

Note: To avoid other dietary factors' effects on the outcomes, the nutrient contents of both raw and hydrolyzed pea seed coats (PSC) were analyzed (data not shown). The amount of added PSC was calculated to ensure diets are equal in total fat (20.0% w/w), protein (27.9% w/w), carbohydrate (35.8% w/w) and fibre (10.0% w/w) and thus are equal in caloric density, except for LFD (total fat 6.0% w/w, protein 27.9% w/w, carbohydrate 49.9% w/w, and fibre 10.0% w/w). PAC content was 435.9 mg/100 g unprocessed PSC.

Example 2: Animal Feeding Trial

Male Sprague-Dawley rats (n=84) were obtained from Charles River Canada (St. Constant, QC) at 8 wk of age and housed 2 per cage. All the animals had 1 wk of acclimatization with access to standard chow and water ad libitum. Then they were randomized into 4 groups, i.e. high fat diet (HFD), low fat diet (LFD), PAC-supplemented HFD (PAC), and HPAC-supplemented HFD (HPAC). LFD group remained on standard chow. All the others were introduced to a 6-week HFD regimen to induce glucose intolerance, which was confirmed using an oral glucose tolerance test (GTT, see Example 3 below). The 4 groups of rats were switched to the experimental diets (Table 1) for 4 wk. Body weights were measured weekly and food intake was recorded daily.

Example 3: Glucose and Insulin Tolerance Tests

Oral (OGTT) or intraperitoneal GTT (IPGTT) was used to determine the status of glucose tolerance in all groups. IPGTT examines the effects of PAC feeding downstream of intestinal absorption factors because the glucose is introduced into the peripheral circulation, bypassing the gut. Seven days before tissue collection, after overnight fasting, all the rats were weighed and baseline blood glucose concentration was measured in whole blood taken from the tail vein with a glucometer (Accu-Check Compact Plus, Roche Diagnostics). Then they received a standard dose of glucose (1 g/kg; oral: 40% w/v, in ddH$_2$O; ip: 20% w/v, in saline), blood glucose was measured at 10, 20, 30, 60, 120 min. Additional blood samples were collected at the same time points to obtain plasma and stored at −80° C. until assayed for insulin and glucagon. Incremental area under the curve (IAUC) was calculated as described [30].

Insulin tolerance tests (ITT) were conducted 1-2 days before the day of tissue collection. After 4-hour fasting, all the rats were weighed and baseline blood glucose level was measured in whole blood with a glucometer. After receiving insulin (0.5 U/kg, ip), blood glucose was measured at 15, 30, 60, 90, 120 min.

Example 4: Tissue Collection

Fed or 16-hour fasted rats were euthanized under anaesthesia (pentobarbital sodium 60 mg/kg, ip) by exsanguination. Blood (5-10 ml) was obtained from the abdominal aorta and divided for preparation of plasma and serum, which were frozen at −80° C. Pancreatic islets were isolated and cultured overnight for insulin secretion studies as previous described [31,32]; an additional pancreas sample just adjacent to the spleen was fixed in formalin overnight for embedding in paraffin by standard techniques.

Example 5: Soluble PAC and Anthocyanin Quantitation

The total extractable PAC content of the native 'Solido' PSC fraction was determined by the butanol-HCl—Fe$^{3+}$ method [28]. Approximately 25 mg subsamples of seed coat tissue (lyophilized and ground to a fine powder using a Retsch ZM 200 mill (PA, USA) with 0.5 mm screen filter) were weighed into 15 mL Falcon tubes. The samples were extracted with 10 ml of 80% methanol for 24 h with shaking. After vortexing the slurry and centrifuging for 5 min at 4000 rpm, the supernatants were used for PAC analysis using the method of Porter et al. [28]. In brief, 2 mL of the butanol: HCl reagent and 66.75 µL of iron reagent were added into a 15 mL glass culture tube. Then, 0.5 mL of clear sample extract was added to the tube and the mixture was vortexed. Two 350 µL aliquots of this solution were removed for use as sample blanks, and the remaining solution was placed into a 95° C. water bath. After 40 min, the solution was allowed to cool at room temperature for 30 min. The reaction products, sample blanks, and a PAC standard curve dilution series were monitored for absorbance at 550 nm using a 96 well UV plate reader (Spectra Max 190, Molecular Devices, CA, USA). The PAC standard solution used was an extract from 'CDC Acer' PSC purified as described by Jin [29].

The high pressure liquid chromatography (HPLC)-photodiode array detection method of Zifkin et al. [33] was used to quantify anthocyanidins in the HPAC fraction.

Example 6: Analysis of PAC-Derived Compounds in PSC and Serum Samples

A. Pea Seed Coats
PSC (25 mg, PAC or HPAC) were extracted in 1 mL methanol for 4 h at −20° C. The supernatant was collected and injected into a HILIC Column (TSKgel Amide-80) for separation. The continuous gradient segments for HILIC (A: 10 mM NH$_4$AC in H$_2$O; B: 10 mM NH$_4$AC in acetonitrile) were: t=0 min, 90% B; t=5 min, 10% B; t=10 min, 10% B; t=30 min, 90% B. The flow rate was 100 µl/min. The flow was directed to the electrospray ionization (ESI) source of a Bruker Impact HD quadrupole time-of-flight (Q-TOF) mass spectrometer (MS). Parameters for analysis were set using HILIC-negative ion mode with spectra acquired over a mass range from m/z 50 to 800. The optimum values of the ESI-MS parameters were: collision energy, 22 eV for catechin derivatives and 25 eV for delphinidin derivatives; collision RF, 700.0 Vpp; transfer time, 30.0 μs; pre-pulse storage, 8.0 μs. The MS data were checked by Bruker's DataAnalyst 4.2.

B. Serum Samples

Proteins in the serum samples were precipitated with 100% methanol (1:3, v/v) at room temperature, and the supernatant was collected and analyzed using Q-TOF MS linked to an HILIC column as described above.

Example 7: Analysis of Plasma Insulin and Glucagon

Plasma samples obtained during the GTT and tissue collection were analysed in duplicate for insulin and glucagon by ELISA using commercial assay kits according to the manufacturer's instructions (rat insulin ELISA, Alpco Diagnostics, Salem, N.H.; glucagon EIA kit, SCETI K.K., Tokyo, JP).

Example 8: Immunohistochemistry

Immunohistochemical staining (IHC) was performed as previously described for determination of α- and β-cell areas [27]. Primary antibodies and their dilutions were as follows: guinea pig anti-insulin, 1:200 (Dako, Burlington, Canada) and rabbit anti-glucagon, 1:200 (Millipore, Billerica, Mass.). Secondary antibodies were HRP-conjugated rabbit anti-guinea pig, 1:200 (Sigma, Oakville, Canada) and goat anti-rabbit, 1:200 (Sigma), respectively. Positive immunoreactivity was visualized by diaminobenzidine plus hydrogen peroxide. Slides were then dehydrated and mounted for photography using an Axiovert microscope equipped with Axiovision 4.7 software (Zeiss). The total pancreatic area (excluding large ducts and veins), the insulin- and glucagon-positive areas were quantified using ImageJ [27].

Example 9: Glucose Stimulated Insulin Secretion from Isolated Islets

To measure insulin release, 3 islets/vial were incubated in Dulbecco's Modified Eagle's medium with low or high glucose concentrations (2.8, 16.5 mM) for 2 h at 37° C. Supernatants were retained and insulin remaining in the islets was extracted with 3% acetic acid, then stored at −20° C. for future insulin radioimmunoas say (RIA) [34]. Total islet insulin content was calculated by adding insulin secreted into supernatant plus that remaining in the islet pellet, as determined by RIA. From this, the percentage of total insulin secreted was calculated for each data point to eliminate variance caused by islet size. Insulin stimulation index was calculated as the ratio of insulin percentage release in response to 16.5 mM glucose versus 2.8 mM glucose.

Example 10: Statistical Analyses

All data were expressed as means±SE, and n represented the number of rats. Multiple groups were analyzed by one-way or two-way analysis of variance followed by Bonferroni's multiple comparison, as appropriate. At $P<0.05$, differences were considered significant. Statistical analyses were performed using GraphPad Prism for Windows version 6.0 (GraphPad Software, San Diego, Calif.).

Example 11: Hydrolysis Depolymerized PAC and Increased Metabolites in Serum

Figure 6B:
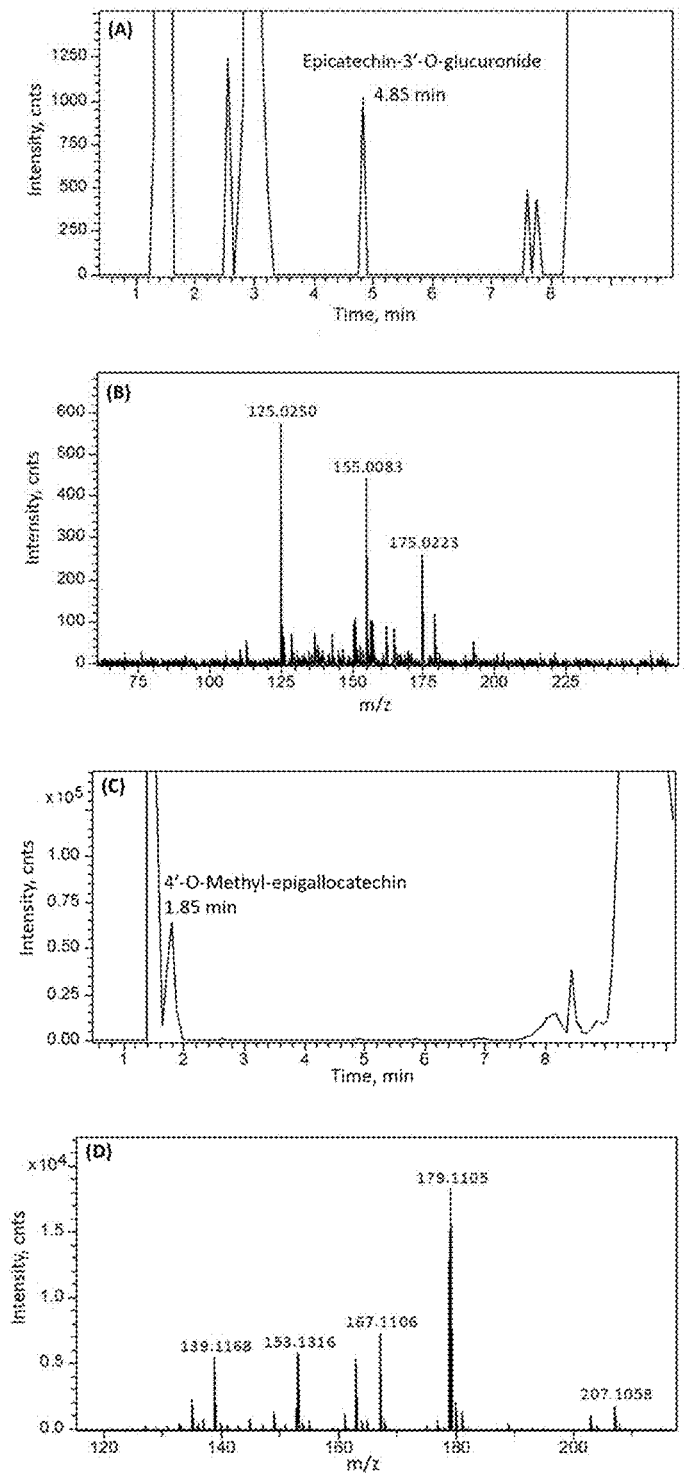
FIG. 6B: ESI-MS spectrum of the HPAC serum extract identifying epicatechin-3'-O-glucuronide and 4'-O-methyl-epigallocatechin. (A) Total ion chromatogram in negative MS/MS mode with precursor ion mass 465.1038; (B) Product ion spectrum of the 4.85 min peak which belongs to epicatechin-3'-O-glucuronide; (C) Total ion chromatogram in negative MS/MS mode with precursor ion mass 319.0823; (D) Product ion spectrum of the 1.85 min peak which belongs to 4'-O-methyl-epigallocatechin.

The total PAC content of the native 'Solido' PSC was 4.51±0.05 mg/100 mg dry weight of sample, n=3) as determined by the butanol-HCl—$Fe^{3+}$ method. Jin [29] found that in the PSC of 'Solido' the PAC flavan-3-ol extension units were nearly exclusively prodelphinidin, while epigallocatechin was the most abundant flavan-3-ol extension subunit followed by gallocatechin. The PAC terminal subunits of this pea cultivar also mainly consisted of gallocatechin and epigallocatechin. Upon acid hydrolysis, the epigallocatechin and gallocatechin were converted to the anthocyanidin delphinidin (FIG. 6A) with a yield of 43±4.9 mg/100 g dwt (n=3; HPAC fraction delphinidin content).

Further characterization of the PAC and HPAC fractions by ESI-MS/MS found that PAC dimers (prodelphinidin A1 and B; FIG. 6) were present in the PAC fraction, but were not present in the HPAC fraction (Table 2), showing that the acid hydrolysis procedure had effectively cleaved the PAC dimers to monomers.

TABLE 2

PAC-derived compounds in pea seed coats and rat serum as detected by ESI-MS/MS.

| | Compound | Retention Time (min) | Precursor Ion Mass (Da) | Main Product Ion | | |
|---|---|---|---|---|---|---|
| | | | | Ion Mass (Da) | Absolute Intensity (cnts) | |
| | | | | | PAC | HPAC |
| Standards | Epicatechin | 1.85 | 289.0673 | 125.0259 | — | — |
| | Gallocatechin | 2.89 | 305.0649 | 179.1105 | — | — |
| | Delphinidin | 12.23 | 301.0335 | 125.0259 | — | — |
| Pea Seed Coats | Prodelphinidin A1 | 5.98 | 607.1093 | 125.0256 | 704 | ND |
| | Prodelphinidin B | 6.31 | 609.1250 | 125.0256 | 1303 | ND |
| | Delphinidin | 12.24 | 301.0335 | 125.0261 | 893 | 6075 |
| Serum | Epicatechin-3'-O-glucuronide | 4.85 | 465.1038 | 125.0250 | ND | 573 |
| | 4'-O-Methyl-epigallocatechin | 1.85 | 319.0823 | 179.1105 | ND | 18197 |

ND, not detected.

High DP is the main factor limiting the absorption of PAC. Therefore, it was expected that PAC-hydrolyzed products would be readily absorbed into the body. To determine and compare the bioavailability between PAC and HPAC, PAC-related metabolites in non-fasted serum samples were analyzed using ESI-MS/MS. 4'-O-methyl-epigallocatechin (the major metabolite) and epicatechin-3'-O-glucuronide were detected in serum samples from HPAC but not PAC (Table 2; for structures see FIG. 6A and FIG. 6B for ESI-MS spectrum). Using the data of 'Solido' PAC composition reported by Jin [29], we conclude that the 4'-O-methyl-epigallocatechin PAC-derived metabolite originated from the flavan-3-ol epigallocatechin extension/terminal units of the hydrolyzed PAC, and epicatechin-3'-O-glucuronide was derived from the terminal units of the hydrolyzed PAC.

Example 12: HPAC Improved Body Composition without Affecting Food Intake

All the rats had similar body weights at both baseline and prior to diet change. Differences in body weights among groups became apparent after switching to the experimental diets as shown in FIG. 1. At the end of the feeding trial, rats in the HPAC group had approximately 18% less weight gain compared to HFD group (HPAC, 139.3±17.0; HFD, 156.9±12.0, %, P<0.05). HPAC group percentage of body fat was ~6% lower versus HFD (P<0.05, Table 3). In contrast, although rats fed PAC-supplemented diet gained ~10% less weight, their body composition was similar to HFD (Table 3). Lean mass was similar in all groups.

PAC contribute to the bitter and astringent tastes of food [21], which may affect food intake of the different experimental groups. However, PAC or HPAC supplementation did not affect food or energy intake compared with HFD (Table 3). LFD rats achieved similar energy intake via increased food intake (Table 3).

Insulin-glucose IAUC index is the product of IAUCs of insulin and glucose response curves and is an index for insulin resistance (IR) in which a higher value suggests higher degree of IR [35,36]. HPAC and LFD both had lower values of insulin-glucose IAUC index compared to HFD (P<0.05), whereas PAC was similar to HFD.

ITT was also used to assess the degree of insulin resistance. Results from ITT (FIG. 3) also support that HPAC were less insulin resistant than HFD rats. Although glucose levels (present as percentage of baseline glucose) responding to insulin administration (FIG. 3A) were similar among all groups during the first 30 min, HPAC had significantly (P<0.05) lower glucose concentrations from 90 to 120 min. PAC also tended to have a slower glucose recovery rate, with a significantly lower glucose concentration at 120 min compared to HFD. Slopes of ITT for 60-120 min were calculated [37] as a direct measurement of glucose recovery rate. Both of the pea seed coat-supplemented groups, especially HPAC, had smaller slopes than HFD, suggesting slower glucose recovery rate (FIG. 3B).

Example 14: HPAC Preserved Pancreatic Islet Morphology and Function

The lowered insulin responses in HPAC during IPGTT might be the result of a smaller β-cell mass. Therefore β-cell and α-cell areas were quantified as an estimate of islet cell mass. Representative photomicrographs are shown in FIGS. 4A and 4B. Pancreatic β-cell area was not different between groups (P=0.4, FIG. 4C). A ~80% decrease (P<0.05) in pancreatic α-cell areas in HPAC was found (FIG. 4D),

TABLE 3

Food intake and body composition

|  | HFD | PAC | HPAC | LFD |
| --- | --- | --- | --- | --- |
| Food Intake (g/rat/d) | 31.25 ± 1.14 | 41.63 ± 2.86 | 39.81 ± 3.34 | 42.50 ± 2.82* |
| Energy Intake (kcal/rat/d) | 134.40 ± 4.91 | 179.0 ± 12.30 | 171.2 ± 14.37 | 153.0 ± 10.15 |
| Fat mass/Final Wt, % | 16.8 ± 1.2 | 15.0 ± 1.2 | 11.3 ± 0.9* | 13.8 ± 1.4 |
| Lean mass/Final Wt, % | 67.0 ± 1.0 | 69.2 ± 1.0 | 70.8 ± 0.9* | 69.4 ± 0.6 |
| Fat mass/Lean mass | 0.26 ± 0.02 | 0.21 ± 0.02 | 0.16 ± 0.01* | 0.19 ± 0.02 |

Values are means ± standard error,
*P < 0.05, compared to HFD, Bonferroni's multiple comparison.

Example 13: HPAC Diet Improved Insulin Resistance Induced by HFD

Seven days prior to tissue collection, IPGTT was performed to compare the effects of different diets on glucose homeostasis. Data are shown as the glucose and insulin responses at each time point (FIGS. 2A and 2C) and as incremental area under the curve (IAUC, FIGS. 2B and 2D). In response to a standard dose of glucose, LFD group had overall lower glucose excursion compared to HFD, with ~50% decrease in IAUC of blood glucose (P<0.01). HPAC had significantly lower blood glucose than HFD at 10 min (P<0.05) and an approximately 25% reduction in IAUC, such that the overall glucose excursion was similar to LFD. Insulin responses in HPAC were much lower at 20 and 30 min, resulting in a significantly lower IAUC (P<0.05) than HFD. Those results indicate improved glucose disposal in HPAC. In contrast, PAC showed similar glucose and insulin responses compared with HFD, suggesting little improvement in glucose intolerance.

which contributed to significantly different cell composition (α/β cell ratio) in pancreatic islets of HPAC (FIG. 4E, P<0.05). Fasting plasma insulin and glucagon concentrations were not different among groups (FIG. 4F, P=0.070; FIG. 4G, P=0.088).

To further examine the effects of PAC and HPAC on pancreatic islet function, and to exclude the possibility that the lower insulin response during IPGTT was caused by impaired insulin secretion from pancreatic islets, GSIS was conducted on isolated islets. As shown in FIG. 5A, insulin secretion in response to 2.8 mM glucose was similar among all groups. When stimulated with 16.5 mM glucose, % release of insulin in HPAC was increased ~3-fold compared to both HFD and PAC. Insulin stimulation indices were significantly different among all groups (FIG. 5B, P=0.047), and HPAC had the highest mean value, indicating ameliorated pancreatic islet function in HPAC. Also there was a trend (FIG. 5C, P=0.126) towards lower insulin content in HPAC.

II. Cooking and Freeze-Drying Enhances Glucose-Lowering Effects of PSC

Example 15: Animals and Diets

All animal care protocols comply with the guidelines of the Canadian Council on Animal Care. They were also reviewed and approved by the Health Sciences Animal Care and Use Committee at the University of Alberta. Eight-week old male Sprague Dawley rats were purchased from the Department of Biology, University of Alberta or Charles River Canada (St. Constant, QC). They were housed two per cage with ad libitum access to normal chow and water for one week. After acclimatization, rats received 6 weeks of high fat control diet (HFD, 20% w/w) to induce insulin resistance, except for the low fat diet (LFD) control group, which remained on chow. The HFD-fed rats were then randomly assigned to the following 3 diets: high fat diet (HFD), raw pea seed coat (RP, HFD supplemented with raw seed coats), cooked pea seed coat (CP, HFD supplemented with cooked seed coats). All these diet groups were isocaloric and maintained a macronutrient ratio of 40:40:20 for fat, carbohydrate and protein. The chow fed rats were put on low fat diet (LFD, 6% w/w), in which carbohydrate replaced the fat. In the treatment groups, the fibre source, which was 10% w/w cellulose in HFD and LFD, was replaced by prepared pea seed coat fractions so that the total fibre weight per gram of chow was identical (Table 4). The protein was adjusted as necessary to ensure the diets were isonitrogenous. The animals were on the pea seed coat diets for four weeks with ad libitum access to food and water.

TABLE 4

Diet Composition (g/kg).

| | HFD | HFD + PSC | LFD |
|---|---|---|---|
| Canola Sterine | 99.5 | 99.5 | 29.85 |
| Flaxseed Oil | 6 | 6 | 1.8 |
| Sunflower Oil | 94.5 | 94.5 | 28.35 |
| Casein | 270 | 263 | 270 |
| Dextrose | 189 | 189 | 255 |
| Corn Starch | 169 | 169 | 245 |
| Cellulose | 100 | 0 | 100 |
| Pea seed coat | 0 | 143 | 0 |
| L-methionine | 2.5 | 2.5 | 2.5 |
| Essential Nutrients | 70.1 | 70.1 | 67.7 |
| Total weight (g) | 1000.6 | 1036.6 | 1000.2 |
| Carbohydrate % | 35.7 | 34.6 | 50 |
| Fat % | 20 | 20 | 6 |
| Protein % | 27.8 | 27.8 | 27.8 |
| Fibre % | 10 | 10 | 10 |

HFD, high fat diet; HFD + PSC, high fat diet supplemented with pea seed coats; LFD, low fat diet.

Example 16: Pea Seed Coat Preparation and Analysis

Seed Coat Preparation

The pea seed coat fractions used in this study were produced from the seeds of the pea (*Pisum sativum* L.) cultivar Canstar that were grown in Alberta, Canada. 'Canstar' is a yellow-seeded field pea cultivar with little to no proanthocyanidins present in its seed coats. The whole pea seeds were dehulled (seed coats removed) using a mechanical dehuller at Agri-Food Discovery Place, University of Alberta. The smaller seed fragments were removed from the bulk seed coat sample using a 1.0 mm screen (Canadian Standard sieve series #18, W.S. Tyler Co. of Canada, St. Catherines, ON). The cleaned seed coats were then ground into a powder using a standard electric coffee grinder for rat feeding studies. A portion of the ground samples were used unprocessed (raw seed coat material) and a portion was subjected to a cooking treatment (cooked seed coat material) which consisted of boiling the samples at 100° C. in deionized water (approximately 10 volumes of water to 1 volume of seed sample) for 30 min. After 30 min of cooking, the samples were cooled down to room temperature and stored at −20° C. until lyophilization of samples (using a freeze dryer; Virtis Ultra 35 L Freeze Dryer, Stone Ridge, N.Y., United States) for 7 days. For starch, protein, and fibre analyses, both raw seed coat and cooked seed coat material were lyophilized for 7 days and further ground using a Retsch, ZM 200 (PA, USA) mill to produce finely ground powder that passed through a 0.5 mm screen.

Starch and Protein Analysis

The ground lyophilized samples were assayed for total starch content using the Total Starch Assay Procedure AA/AMG 11/01 (Megazyme International Ireland, Ltd, Bray, Ireland; AOAC Method 996.11). A nitrogen analyzer (LECO TruSpec CN Carbon/Nitrogen Determinator; Leco Corporation; St. Joseph, Mich.) was used to estimate the total protein content in the lyophilized ground seed coat samples. Total protein content of the seed coats was calculated by multiplying the nitrogen content with a conversion factor of 6.25 (AOAC method 968.06). Caffeine (150 mg) and EDTA (Ethylenediaminetetraacetic acid; 100 mg) were used as standards for instrument calibration.

Non-Starch Polysaccharides (NSP) Analysis (Fibre)

The total, water insoluble and soluble non-starch polysaccharide (fibre) components of seed coats were determined using the methods described in Englyst and Hudson (1987) and Englyst (1989). Briefly, for hydrolysis and removal of starch from the seed coat material, 45 to 50 mg of ground sample was incubated with DMSO (dimethyl sulphoxide; 0.25 mL) at 100° C. in a water bath for 1 h. The sample was immediately transferred to a 42° C. water bath, then sodium acetate buffer (1 mL; 0.1M, pH 5.2), aqueous pancreatin solution (100 µL; 25 mg/mL; pancreatin from porcine pancreas; 8×U.S.P., Sigma Co.) and aqueous pullulanase solution (50 µL; 0.0165 enzyme units) were added, vortexed, and incubated for 16 hours.

The resulting starch-free residue was processed for total and insoluble NSP determination in independent samples (two replicates per sample). For total NSP analysis, ethanol (95%, 6 mL) was added to a starch-free residue sample, followed by vortexing and incubation for 1 h at room temperature. Subsequently, the solution was centrifuged at 1914 g for 20 min and the supernatant was removed by aspiration. The residue was washed twice with ethanol (85%; 5 mL) and then placed into a 65° C. water bath until the residue was dry.

For insoluble NSP analysis, phosphate buffer (0.2 M, pH 7.0; 6 mL) was added to a starch-free residue sample, then the sample was vortexed and heated for 1 h in a 100° C. water bath. Subsequently, the solution was centrifuged at 1914 g for 20 minutes and the supernatant was removed by aspiration. The residue was washed with ethanol (85%; 5 mL), then phosphate buffer (0.2 M, pH 7.0; 5 mL), and then placed into a 65° C. water bath until the residue was dry.

The following steps were performed on the dry total NSP and insoluble NSP residue samples. The dried starch-free residue was dispersed in $H_2SO_4$ (12 M; 0.5 mL) and incubated in a 35° C. water bath for 1 h. Subsequently, distilled water (5.5 mL) was added to the sample slurry followed by vortexing, and the solution was placed in a 100° C. water bath for 2 h. The resulting hydrolysate solution was then cooled to room temperature and aqueous myo-inositol (20 mg/mL; 0.1 mL) was added as an external standard. For conversion of the hydrolyzed sugars to their alditol acetates, the hydrolysate was vortexed and centrifuged at 2000 g for 5 min. $NH_4OH$ (12 M 0.2 mL; 12 M) was added to a 1 mL aliquot of the hydrolysate and the mixture was vortexed, then freshly prepared $NaBH_4$ solution (0.1 mL; 100 mg $NaBH_4$ per mL of 3 M aq $NH_4OH$ solution) was added and the solution was incubated for 1 h in a 40° C. water bath. Subsequently, glacial acetic acid (0.1 mL) was added to the solution, followed by vortexing. A 0.2 mL aliquot of the acidified solution was added to 0.3 mL 1-methylimidazole. Acetic anhydride (2 mL) was then added to this solution and vortexed continuously for 10 min. Distilled water (5 mL) was subsequently added to the solution to decompose excess acetic anhydride and aid in phase separation. After the solution was cooled to room temperature, dichloromethane (4 mL) was added and mixed for 15 sec. After centrifugation at 700 g for 5 min, the top layer was aspirated off and distilled water (5 mL) was added. The solution was again centrifuged at 700 g for 5 minutes, the top layer was aspirated off, and the bottom layer was dried in a 50° C. evaporator. Dichloromethane (1 mL) was added to the residue and a 0.5 µL aliquot of the derivatized sample was injected onto a DB-17 fused silica capillary column (0.25 mm i.d.×30 m; J&W Scientific, Folsom, Calif.) connected to a Varian 3400 gas chromatograph equipped with a cool-on-column injector. Helium was used as the carrier gas with a flow rate of 1.5 mL/min. The injector temperature was increased from 60° C. to 270° C. at the rate of 150° C./min and maintained for 20 min. Oven temperature was raised from 50° C. to 190° C. at a rate of 30° C./min, and maintained for 3 min, then increased to 270° C. at the rate of 5° C./min, and maintained for 5 min. The flame ionization detector (FID) temperature was set at 270° C. Peak area integration for carbohydrate analyses were according to a Shimadzu Ezchrom Data System (Shimadzu Scientific Instruments Inc., Columbia, Md.). The soluble NSP values were estimated by subtracting the insoluble NSP value from the total NSP value for a given sample.

Example 17: Glucose and Insulin Tolerance Tests

After 3 weeks of experimental diets (9 weeks in total on HFD), rats were appointed to either an oral glucose tolerance test (oGTT) or an intraperitoneal glucose tolerance test (ipGTT). The tests were performed following an overnight fast. Fasting blood glucose was measured and blood was collected from a tail vein for insulin determination. Then, each rat received 1 g of glucose per kg of body weight via oral administration or intraperitoneal injections. Blood glucose values were obtained at 10, 20, 30, 60, and 120 minutes, using a glucometer (Accu-Check Compact Plus, Roche Diagnostics, Laval, QC). About 50 µl of blood was taken at each time point during ipGTT and centrifuged to obtain serum, which was stored at −20° C. Dipeptidyl peptidase (DPP)-IV inhibitor (Millipore, Billerica, Mass.) was added to aliquots obtained at baseline and 30 minutes in order to assay gastric inhibitory polypeptide (GIP). Insulin tolerance test was conducted at the end of the fourth week, during which animal received an intraperitoneal injection of 20 µg/kg dose of insulin, and blood glucose was determined at 0, 15, 30, 60, 90 & 120 minutes. Area under the curve (AUC) and incremental area under the curve (IAUC) were calculated in accordance with established methods (Wolever, 2004).

Example 18: Body Weight, Food Intake and Measurement of Body Composition

Body weights were measured on a weekly basis. After introduction of the supplemented diets, food intake was measured for 24 hours twice during the 4-week period. In addition, one day prior to tissue collection, magnetic resonance imaging (MRI) technique was applied to specify lean and fat mass body composition using an EchoMRI Whole Body Composition Analyzer (Echo Medical Systems LLC, Houston, Tex.).

Example 19: Tissue Collection

At the end of the 10th week, animals were euthanized by an overdose of xylazine/ketamine via ip injection. A 3-5 mL blood sample was obtained by cardiac puncture and serum obtained following centrifugation, which was then stored at −80° C. Intestinal segments and pancreatic tissue were collected and fixed in buffered formalin, dehydrated in graded ethanol and embedded in paraffin. They were then cut to generate 5 µm cross sections using a microtome, and adhered to glass slides.

Example 20: Assays of Serum

Samples from the ipGTT were assayed for insulin using an ELISA kit (Alpco Diagnostics, Salem, N.H.). GIP was assayed by Meso Scale Discovery human total GIP kit (validated for use with rat samples). Serum obtained at euthanasia was assayed for triglyceride (Serum Triglyceride Determination Kit, Sigma-Aldrich) and free fatty acids (Waco Diagnostics, Richmond, Va.) by colourimetric assays and active glucagon-like peptide-1 by ELISA (Millipore, Billerica, Mass.) according to manufacturers' instructions.

Example 21: Immunohistochemistry and Morphometric Tissue Analysis

Tissue slides were rehydrated and endogenous peroxidases quenched using techniques described previously (Whitlock et al., 2012). Non-specific binding was reduced by blocking with appropriate non-immune sera (1:20 dilution in PBS) for twenty minutes at room temperature. For pancreas, rabbit anti-glucagon (Linco) and guinea pig anti-insulin primary antibodies (Dako) were diluted 1:100 in PBS, applied to the tissue sections and incubated overnight at 4° C. For jejunum and ileum, mouse anti-GIP (generously provided by University of British Columbia) and rabbit anti-GLP-1 (Epitomics, Burlingame, Calif.) were respectively diluted 1:1000 and 1:250 in PBS, then applied and incubated under the same conditions. Following washes, appropriate peroxidase-coupled secondary antibodies (1:200) were applied to the sections and the slides were incubated for 1 hour at room temperature. Positive reactions were identified by peroxidation of diaminobenzidene in the presence of $H_2O_2$. Imaging was performed using an Axiovert microscope connected to an AxioCam MRm digital camera (Carl Zeiss, TO, Ontario, Canada), and controlled with AxioVision 4.6 software.

For pancreas, each section of the tissue was photographed under ten times magnification and then total pancreatic tissue area as well as alpha- and beta-cell areas were quantified by ImageJ software. The ratios of the alpha-cell and beta-cell to total pancreatic area were calculated for each rat. For jejunum and ileum, random sections of each tissue were selected and photographed under twenty times magnification, and total number of GIP-positive and GLP-1-positive cells were calculated. The number of positive cells was then normalized to the number of villus.

Example 22: Quantification of Glucose Transporter Gene Expression (Glut2, Glut5, SGLT1)

Total RNA was isolated from ileal tissue using Trizol reagent and purified with an RNeasy Mini Kit (Qiagen, Valencia, Calif.) per manufacturer's instructions. The complementary DNA (cDNA) was generated from RNA samples using a cloned AMV first-strand cDNA synthesis kit (Invitrogen). The cDNA samples were amplified using primers synthesized by the IBD core at the University of Alberta and analyzed by quantitative reverse transcription polymerase chain reaction (qRT-PCR). Primer sequences used for amplifications were as follows: Glut2 (Accession Number NM_012879) forward primer, 5'-GAC ACC CCA CTC ATA GTC ACA C-3' (SEQ ID NO: 1), Glut2 reverse primer, 5'-CAG CAA TGA TGA GAG CAT GTG-3' (SEQ ID NO: 2), Glut5 (Accession Number NM_031741) forward primer, 5'-AAC TTT CCT AGC TGC CTT TGG CTC-3' (SEQ ID NO: 3), Glut5 reverse primer, 5'-TAG CAG GTG GGA GGT CAT TAA GCT-3' (SEQ ID NO: 4), SGLT-1 (Accession Number NM_013033) forward primer, 5'-ATG GTG TGG TGG CCG ATT GG-3' (SEQ ID NO: 5), SGLT-1 reverse primer, 5'-GTG TAG ATG TCC ATG GTG NAG AG-3' (SEQ ID NO: 6). The housekeeping gene 18S ribosomal RNA was used for normalization (forward primer 5'-AGC GAT TTG TCT GGT TAA TTC CGA TA-3' (SEQ ID NO: 7), reverse primer 5'-CIA AGG GCA TCA CAG ACC TGT TAT TG-3' (SEQ ID NO: 8). All sample reactions were prepared using Evolution Iva Green qPCR mastermix (Montreal Biotech, Montreal, Canada) and run in duplicate on a Corbett Rotor-Gene 6000 cycler.

Example 23: Statistical Analysis

Two-way repeated measures ANOVA was performed on the oGTT, ipGTT, and insulin ELISA data. One-way ANOVA and student t-test were used to compare the other data, as appropriate. All data are expressed as means±SEM; Bonferroni post-test was performed to assess differences between diet groups and a p-value <0.05 was considered to be significant.

Example 24: Fibre Analysis

Analysis of the fibre constituents from raw and cooked pea seed coats is reported in Table 5. The total fibre (NSP) content of the raw seed coat fraction was 68% w/w, with 64-65% composed of insoluble fibre and 3-4% soluble fibre. The total fibre fraction was composed mainly of glucose moieties (52%), while the total and insoluble NSF fibre fraction was also rich in xylose. Arabinose (4%), and mannose (0.2%) were also present in the total fibre of pea seed coats, but at low levels. Consistently, the amount of rhamnose was enriched in the soluble fraction compared to the total and insoluble fibre fractions. Galactose, xylose and a small amount of fucose were also detected in the soluble fibre fraction. The cooking treatment did not affect the fibre classes of the pea seed coats.

TABLE 5

Sugar components of raw, cooked and hydrolyzed seed coats of 'Canstar' by GC analysis

| | Rhamnose | Ribose | Fucose | Arabinose | Xylose | Mannose | Glucose | Galactose | Total |
|---|---|---|---|---|---|---|---|---|---|
| | | | | mg/100 mg dwt (%) | | | | | |
| Raw Seed Coat Fraction | | | | | | | | | |
| Total | 0.73 ± 0.01 | 0.05 ± 0.01 | 0.27 ± 0.02 | 3.73 ± 0.33 | 10.59 ± 0.87 | 0.19 ± 0.01 | 51.81 ± 1.11 | 0.77 ± 0.03 | 68.13 ± 2.04 |
| Insoluble | 0.43 ± 0.05 | 0.02 ± 0.01 | 0.14 ± 0.00 | 2.02 ± 0.12 | 9.99 ± 0.56 | 0.17 ± 0.01 | 52.07 ± 0.65 | 0.43 ± 0.02 | 65.28 ± 0.17 |
| Soluble | 0.30 ± 0.07 | 0.03 ± 0.01 | 0.12 ± 0.02 | 1.71 ± 0.21 | 0.60 ± 0.31 | 0.02 ± 0.00 | 1.00 ± 1.00 | 0.34 ± 0.02 | 4.11 ± 1.50 |
| Cooked Seed Coat Fraction | | | | | | | | | |
| Total | 0.62 ± 0.01 | 0.06 ± 0.01 | 0.25 ± 0.01 | 3.71 ± 0.36 | 10.64 ± 0.91 | 0.20 ± 0.01 | 51.50 ± 0.56 | 0.86 ± 0.05 | 67.84 ± 1.84 |
| Insoluble | 0.34 ± 0.01 | 0.01 ± 0.00 | 0.14 ± 0.01 | 1.76 ± 0.16 | 9.50 ± 0.76 | 0.17 ± 0.00 | 52.64 ± 1.15 | 0.40 ± 0.03 | 64.96 ± 1.97 |
| Soluble | 0.28 ± 0.02 | 0.04 ± 0.01 | 0.11 ± 0.01 | 1.95 ± 0.21 | 1.14 ± 0.15 | 0.03 ± 0.00 | 0.30 ± 0.30 | 0.46 ± 0.07 | 4.33 ± 0.31 |

*Data are means ± standard error of the mean, n = 3.

The total protein content of the raw pea seed coat fraction was 6-7% by weight, and the total starch content was less than 1% (Table 6). Again, the cooking treatment did not affect the total protein or starch content of the pea seed coat fraction.

TABLE 6

Protein and total starch components of raw and cooked pea seed coats of 'Canstar'.

| Pea seed coat | Protein (%) | Total starch (%) |
|---|---|---|
| Raw | 6.65 ± 0.05 | 0.16 ± 0.01 |
| Cooked[a] | 6.91 ± 0.03 | 0.59 ± 0.02 |

[a]placed in boiling water for 30 minutes

% = mg/100 mg dry weight of sample.

Data are means ± SEM, n = 3.

Example 25: Body Weight and Body Composition Analysis

Rats in all groups gained the same amount of weight, calculated as % of baseline, at the end of the study (Table 7, P>0.05). Food intake data were also comparable between groups indicating that the palatability of the diets did not affect the results. MRI data revealed higher fat mass in RP compared with LFD when normalized to total body weight (P<0.05, Table 7).

TABLE 7

Metabolic profile of rats fed diets containing pea fractions.

| | Diet group | | | | | | | |
|---|---|---|---|---|---|---|---|---|
| | HFD | | RP | | CP | | LFD | |
| | Mean | SEM | Mean | SEM | Mean | SEM | Mean | SEM |
| BW (g) Baseline | 401.1 | 11 | 402.2 | 10 | 394.2 | 14.1 | 397 | 13.3 |
| BW (g) Final | 627 | 12.3 | 649.3 | 13.9 | 660.3 | 16.1 | 608 | 14.07 |
| Change (% of baseline BW) | 65.84 | 3.79 | 67.61 | 3.12 | 74.52 | 3.33 | 62.54 | 3.91 |
| Fat mass (% of final BW) | 18.9 | 1.21 | 19.1 | 0.97 | 18.1 | 0.92 | 16.2 | 1.08 |
| Food intake (Kcal/day) | 134.4 | 4.9 | 138.1 | 8.4 | 143 | 14.5 | 153 | 10.2 |
| Fasting blood glucose (mmol/l)$^§$ | 5.3 | 0.18 | 5.5$^a$ | 0.14 | 4.9 | 0.28 | 4.4 | 0.08 |
| Fasting serum insulin (pmol/l)$^§$ | 1.04 | 0.13 | 1.24 | 0.19 | 0.49* | 0.08 | 0.72 | 0.15 |
| Serum TG (mg/dl)$^▪$ | 52.2 | 2.3 | 45.3 | 8.7 | 30.4* | 4.4 | 32.6 | 4.0 |
| Serum NEFA (mmol/l)$^▪$ | 0.5 | 0.1 | 0.49 | 0.07 | 0.37 | 0.09 | 0.37 | 0.08 |
| Fasting serum glucagon (pg/ml)$^▪$ | 308 | 32.31 | 286.6 | 12.28 | 167.5* | 26.9 | 246.7 | 17.61 |
| Fasting serum GLP-1 (pg/ml)$^▪$ | 18.3 | 0.7 | 23.1 | 2.5 | 27.9* | 1.6 | 23.4 | 1.5 |

BW, body weight; HFD, high fat diet; RP, raw pea seed coat (HFD supplemented with raw seed coats); CP, cooked pea seed coat (HFD supplemented with cooked seed coats); LFD, low fat diet; Data are means ± standard error of the mean (SEM), n = 4 to 25.
Asterisks show significant difference compared to HFD (*P < 0.05); Superscript letter indicates significant difference compared to LFD ($^a$P < 0.05); $^§$Blood sampling was done at the end of the feeding trial during oral glucose tolerance test;
$^▪$Serum for TG, NEFA, glucagon and GLP-1 assessment was obtained from blood samples collected from fasted rats by cardiac puncture at the time of tissue collection.

Example 26: Circulating Metabolites and Hormones

Figure 7:
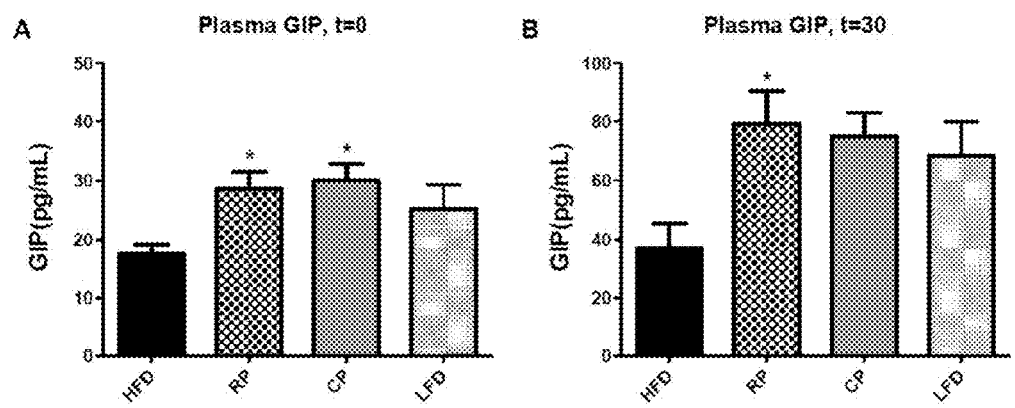
FIG. 7: Plasma gastric inhibitory polypeptide (GIP) concentrations measured during oGTT at fasting (t=0 min), and following administration of 1 g/kg glucose (t=30 min) in rats fed raw (7A) or cooked (7B) pea seed coats. The bars are the mean±SEM, n=4-7. * indicates significant difference compared to HFD (*P<0.05).

Fasting blood glucose was significantly higher in RP than LFD (P<0.05; Table 7). Fasting serum insulin was significantly lower in CP than HFD (P<0.05; Table 8). Serum triglyceride concentrations were significantly higher (P<0.05) in HFD than CP or LFD, but no differences in serum NEFA were detected (Table 8). Serum GLP-1 was significantly higher only in CP compared with HFD (P<0.05; Table 7). As shown in FIG. 7, in fasted rats, fasting serum GIP concentrations were 50% higher in RP and CP than HFD (P<0.05 for both). A similar trend was observed with GIP measured 30 min after glucose administration in the OGTT, in which RP was 2-fold higher than HFD (FIGS. 7A and 7B, P<0.05).

Example 27: Glucose Tolerance Tests and Insulin Tolerance Test

Figure 8:
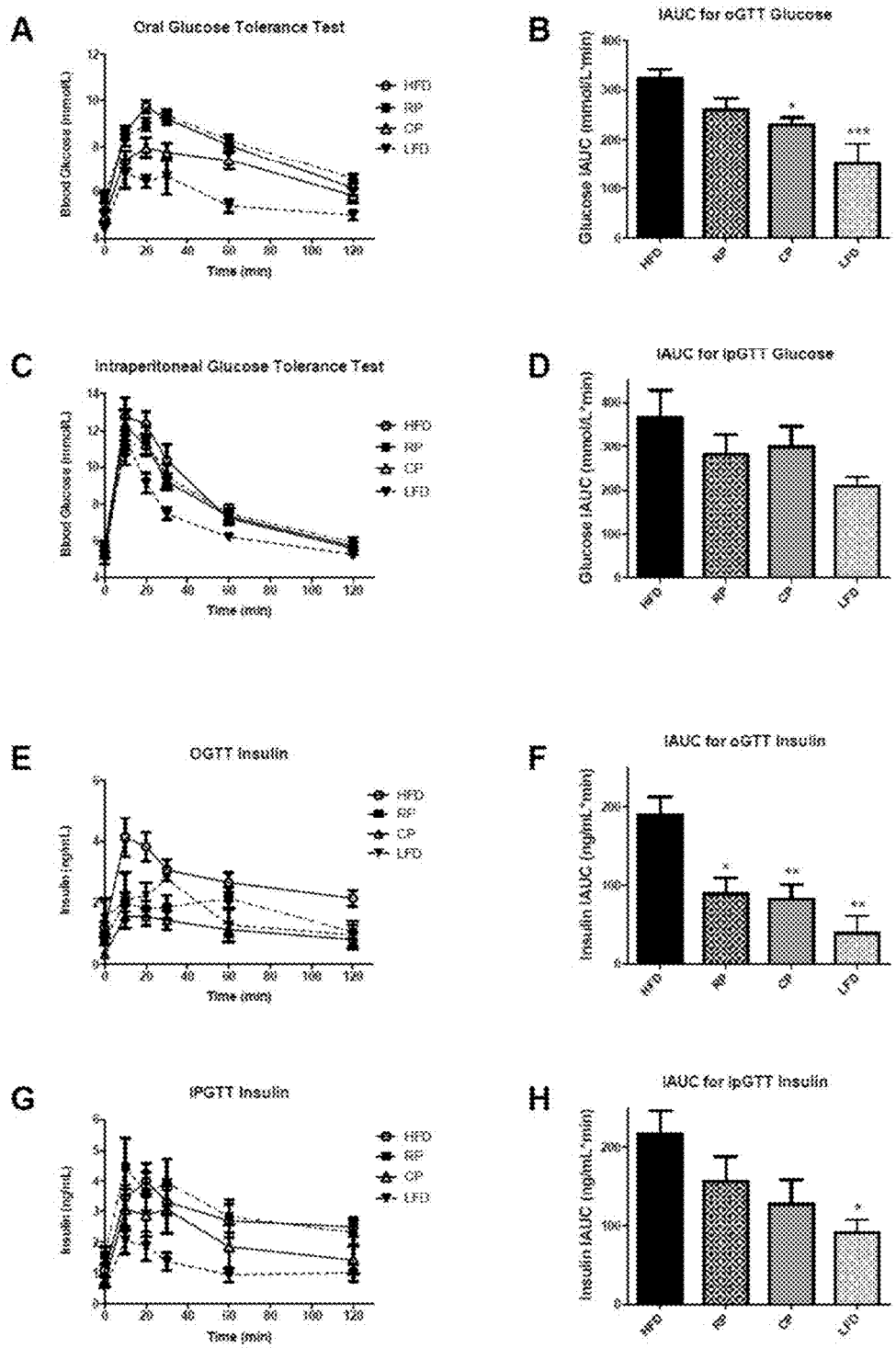
FIG. 8: Effect of feeding PSC on oral and intraperitoneal glucose tolerance in rats fed raw or cooked pea seed coats. (A, C) Effect of 4 weeks of feeding a high fat diet (HFD, 20% w/w) supplemented with raw (RP) or cooked (CP) pea seed coats on blood glucose levels measured basally and following oral or intraperitoneal administration of 1 g/kg glucose. (B, D) Incremental area under the curve (IAUC) was calculated for glucose during oral glucose tolerance test (oGTT) and intraperitoneal glucose tolerance test (ipGTT). (E,G) Plasma insulin levels measured using the blood samples collected during oGTT and ipGTT (baseline and in response to administration of 1 g/kg glucose). (F,H) Incremental area under the curve for insulin during oGTT and ipGTT. The data are means±SEM, n=4-14. Significant differences seen at different time points are explained in the text, while differences between incremental area under the curve (IAUC) are depicted here. Asterisks show significant difference compared to HFD (*P<0.001, P<0.01, *P<0.05).

OGTT and ipGTT results are shown as responses over 120 minutes (FIGS. 8A and 8C), and as incremental area under the curve (IAUC; FIGS. 8B and 8D). As expected, LFD had lower glucose response compared to HFD at t=10 min (P<0.05), and t=20, 30, and 60 min (P<0.001). CP but not RP rats had lower glucose response compared to the HFD group at t=10 (P<0.05), t=20 (P<0.001), and t=30 (P<0.01) min. IAUC during oGTT showed that both CP and LFD groups had glucose values that were significantly lower than HFD (FIG. 2B; P<0.05 and P<0.001, respectively). Although neither CP nor RP had different ipGTT from HFD group (FIG. 8C), LFD had improved response at t=20 (P<0.001) and t=30 (P<0.01) min. Trends for LFD and CP to lower IAUC during ipGTT were attenuated and not statistically significant (FIG. 8D).

Figure 9:
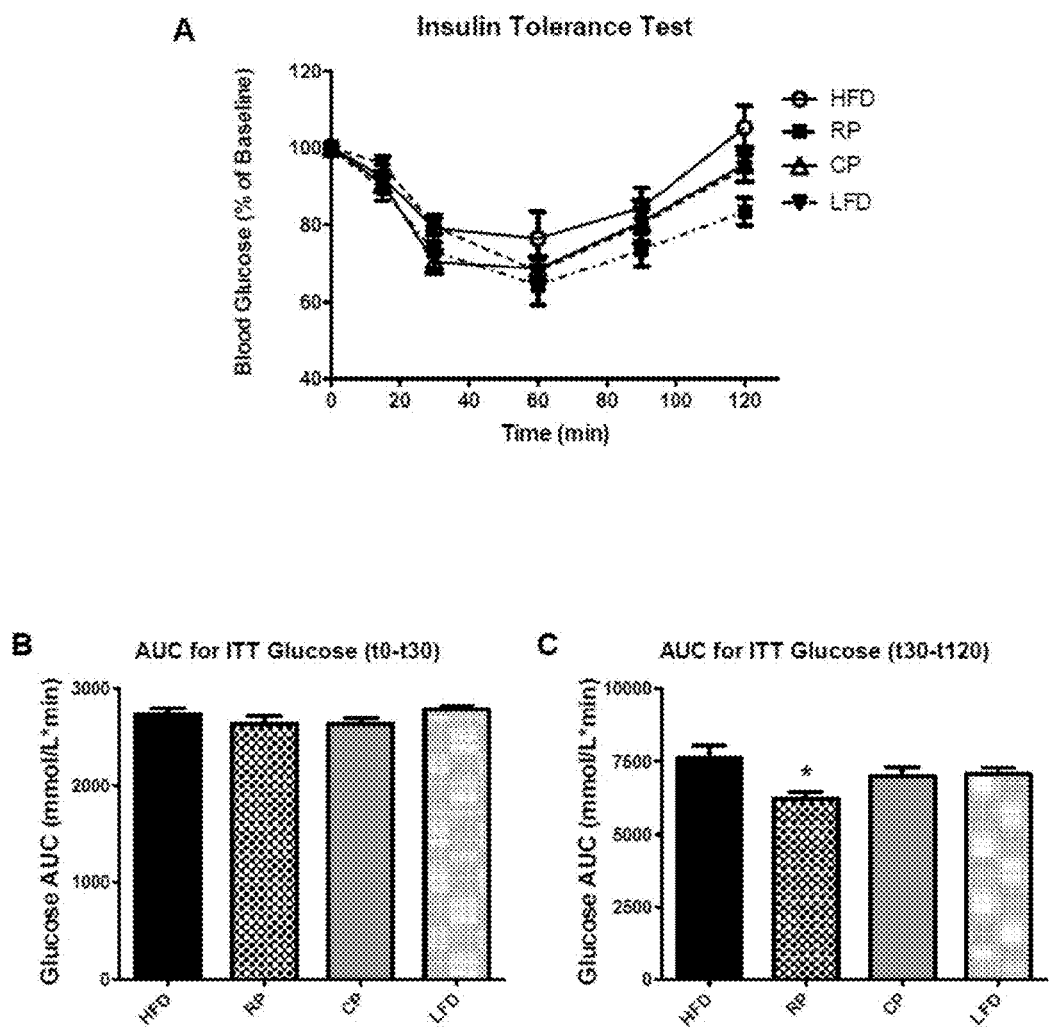
FIG. 9: Insulin tolerance test was performed on rats fed raw or cooked pea seed coats after a 4 hour fast. Blood glucose levels are shown as (A) % of basal glucose, and Area Under the Curve (AUC) from (B) t=0 to t=30 min and (C) t=30 to t=120 min for blood glucose. A significant decrease in glucose for RP compared to HFD was observed at t=30-120 min (*P<0.05). Data are means±SEM, n=8.

During oGTT, RP rats had lower insulin concentrations than HFD rats at t=10 and 20 min (FIG. 8E; P<0.001); CP group had decreased insulin concentrations compared to the HFD group at t=10 (P<0.001), t=20 (P<0.001), t=30 (P<0.01), t=60 (P<0.01) and t=120 (P<0.05) min. The LFD group had lower serum insulin than the HFD group at t=10 (P<0.01) min. Both RP and CP groups had smaller IAUC values when compared to HFD (FIG. 8F; P<0.05 and P<0.01 respectively); LFD rats also had significantly lower IAUC (P<0.01). Insulin concentrations of CP and RP groups during ipGTT were not different than those of HFD (FIG. 8G). However, LFD had decreased concentrations at t=20 and 30 min (P<0.05). IAUC data also only revealed a difference between HFD and LFD (P<0.05) (FIG. 8H). Blood glucose levels during the glucose disappearance phase (0-30 min) of the ITT were comparable among the groups (FIG. 3A,B). During the recovery phase (60-120 min), HFD rats rebounded most quickly and this was significantly faster than for RP rats (P<0.05) (FIG. 9C).

Example 28: Pancreatic Beta- and Alpha-Cell Mass Analysis

Figure 10:
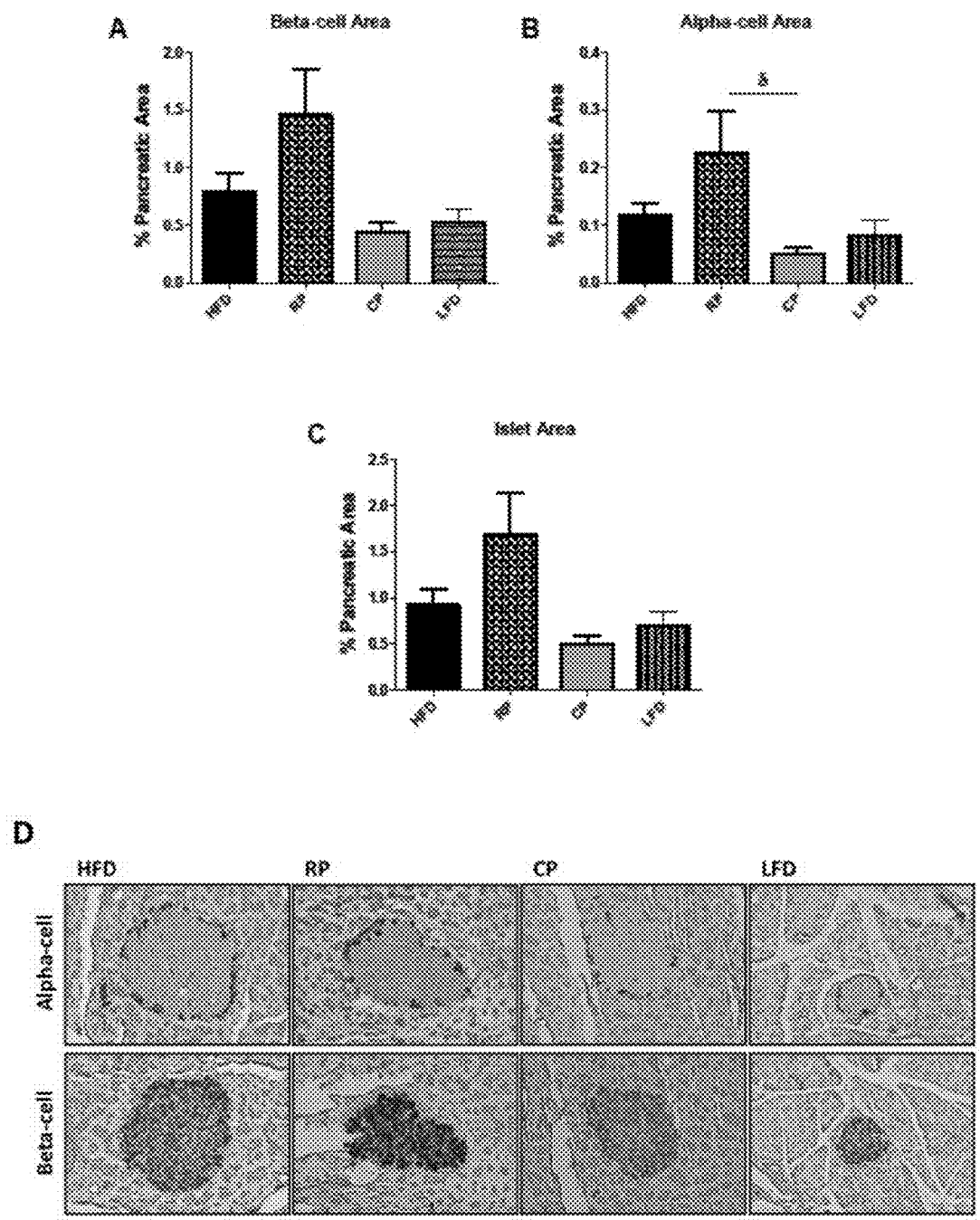
FIG. 10: Beta-cell (A) and alpha-cell (B) areas of rats fed a high fat diet (HFD), raw PSC (RP), cooked PSC (CP) and low fat diet (LFD) for 4 weeks, presented as percentage of pancreatic area. (C) Estimated total islet area. Alpha-cell area was significantly different between the groups (P<0.05), where CP rats revealed a smaller alpha-cell area ($^{b}P<0.05$) when compared to RP. Data are means±SEM, n=6-8. (D) Representative insulin- and glucagon-stained islets of all the groups.

Pancreatic beta- and alpha-cell area at the end of the study are shown in FIGS. 10A and 10B. After four weeks of pea seed coat intervention, no significant difference in beta-cell area between diet groups was observed (FIG. 10A; P>0.05). As shown in FIG. 4B, alpha-cell area in the four diet groups followed a similar pattern with beta-cell area; however, significant differences were found between diet groups (P<0.05), with CP fed rats having a significantly smaller alpha-cell area compared with the RP fed rats (P<0.05). Total islet area was estimated by adding alpha- and beta-cell areas and are presented in FIG. 10C (P=0.16; denoting trend to increased islet area in the RP group). Representative micrographs depicted in FIG. 4D suggest that the increase in islet area of the RP group is due to an increase in the number of islets, rather than the size of individual islets.

Example 29: K- and L-Cell Quantification

Figure 11:
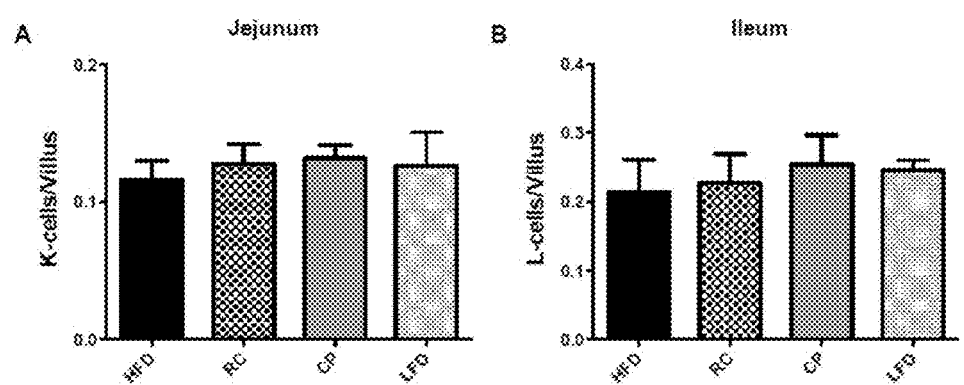
FIG. 11: Number of K-cells (A) and L-cells (B) as detected using GIP and GLP-1 immunoreactivity in jejunum and ileum of rats fed raw or cooked pea seed coats, presented as number of positive cells per villus. Data are means±SEM, n=4. No significant differences were observed.

There was no significant difference in the number of K-cells expressing GIP in the jejunum shown in FIG. 11A (P>0.05). Similarly, the number of GLP-1 positive L-cells in the ileum was comparable between all the groups (FIG. 11B; P>0.05).

Example 30: mRNA Expression of Glucose Transporters

Figure 12:
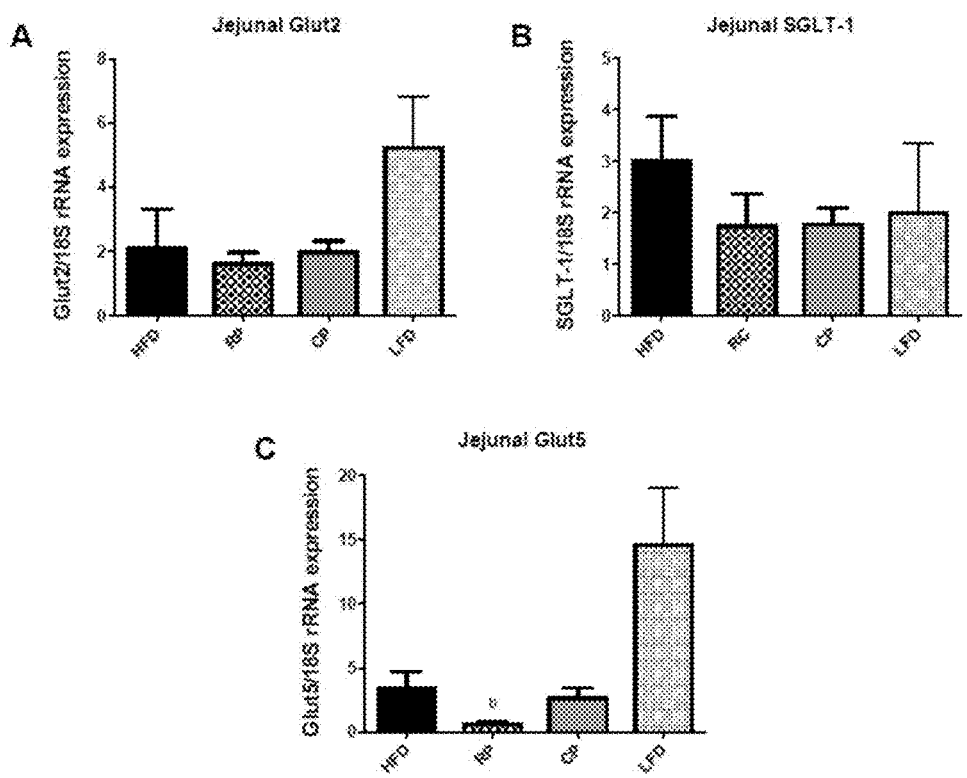
FIG. 12: mRNA expression of Glut2 (A), SGLT1 (B) and Glut5 (C) (normalized to 18S rRNA expression) in jejunum of rats fed raw or cooked pea seed coats. Data are means±SEM, n=5-12. Letter $^{b}$ indicates significant difference compared to LFD ($^{b}P<0.01$).

Jejunal mRNA expression of Glut2 and SGLT1 were similar between the groups (FIGS. 12A and 12B); however, Glut5 expression was significantly different between diet groups (P=0.005), with a higher expression in RP when compared to LFD (FIG. 12C; P<0.01).

The present study demonstrated that supplementing a HFD with cooked pea seed coats improved glucose tolerance, whereas raw seed coat supplementation was not as beneficial. We also observed that the effect of the pea seed coat fibre on postprandial glucose excursions was only detectable when glucose was administered orally and not intraperitoneally. In other words, bypassing the gastrointestinal tract during ipGTT diminished the improved glycemic excursions in the pea fibre groups to a high degree. These divergent outcomes on oral versus ip glucose tolerance led us to consider mechanisms of action involving the gastrointestinal tract.

The total fibre fraction of pea seed coats was mainly composed of the monosaccharide glucose (Table 2), indicating that the most abundant polysaccharide present was cellulose (made up of linear chains of glucose). Because cellulose is a water-insoluble polysaccharide, the insoluble fibre component was also mainly made up of cellulose. The glucose content determined in the total NSP fibre of pea seed coats in this study is consistent with that of 58% reported by Weightman et al. (1994). The higher percentage of xylose (also consistent with Weightman et al. 1994), along with the occurrence of fucose, galactose, and glucose in the total and insoluble NSF fibre fraction is indicative of the presence of the cell wall cellulose microfibril cross-linking polysaccharide, fucogalacto-xyloglucan, commonly found in legume family members (Carpita and McCann, 2002). The presence of arabinose in the total fibre of pea seed coats (Weightman et al., 1994 reported 3.9% arabinose in this fraction) suggests the presence of glucuronoarabinoxylans and/or pectins (Carpita and McCann, 2002). Very low levels of mannose indicate minimal presence of glucomannans, galactoglucomannans, or galactomannans in interlocking microfibrils of the cell wall (Carpita and McCann, 2002). The major non-cellulosic neutral sugars, arabinose and xylose, detected in the soluble fibre pea seed coat fraction indicate the presence of pectin (Weightman et al., 1994; Carpita and McCann, 2002). Rhamnose, which is another constituent of pectins, was also enriched in the soluble fraction of pea seed coats. Galactose, xylose and the small amount of fucose also indicate the presence of fucogalacto-xyloglucans in the soluble fibre fraction.

Cooking treatment improved glucose homeostasis but did not alter the fibre classes of the pea seed coat fraction. One explanation is that the boiling process may have caused separation and/or hydration of the fibre components that were stabilized by the subsequent lyophilization. Our results are consistent with previous studies showing that cooking procedures did not affect the total dietary fibre (Goodlad & Mathers, 1992; Marconi et al., 2000). In another study, however, it was reported that cooking followed by freeze-drying resulted in increased insoluble dietary fibre (IDF) in whole legume seeds (Almeida Costa et al., 2006). Conversely, Kutos et al. (2003), found decreased IDF content when examining the effect of thermal processing on whole beans. Other thermal procedures such as autoclaving have also been shown to result in changes in the composition of wheat bran fibre that lead to less fat accumulation upon consumption (Jones et al., 2014). In addition, boiling may lead to partial solubilization and depolymerization of hemicelluloses and insoluble pectic substances (Marconi et al., 2000), which may change the properties of the fibre with respect to gut fermentation. Altered microstructures of pea flour, as a result of thermal treatments in general, can promote its nutritional and functional characteristics, among which are increased fat and water absorption capacity, and emulsifying and gelling activity (Ma et al., 2011). In addition to higher nutritional value, the thermal processing-derived characteristics of pea flour have been suggested to improve its practicality for food application (Almeida Costa et al., 2006; Ma et al., 2011).

As shown here, enhanced glucose control occurred in the CP group during oGTT versus no improvement during ipGTT. This effect could be explained by several different mechanisms. SDF in general has been proposed to improve glycemic control and insulin sensitivity through mechanisms such as delayed gastric emptying and glucose absorption by increasing gastrointestinal viscosity (Galisteo et al., 2008). In this study however, insulin sensitivity did not appear to be affected by pea seed coat supplementation. SDF can also be fermented to SCFA in the colon, which are absorbed into the blood and are reported to suppress glucose production in the liver (Galisteo et al., 2008) and stimulate skeletal muscle uptake of glucose (Lu et al., 2004). A previous study by our group showed increased circulating 3-hydroxybutyrate believed to be derived from butyrate of dietary origin because butyrate dehydrogenase expression in the liver was suppressed (Chan et al., 2014). On the other hand IDF, in spite of lacking effects on viscosity, has also been shown to have a role in regulating glucose homeostasis (Schenk et al., 2003; Weickert et al., 2006). CP might improve oGTT by down-regulating the expression of intestinal glucose transporters; however, HFD appeared to be the main negative driver of glucose transporter expression, and there was no subsequent modulation upon addition of RP or CP. Contrary to our results, a study performed on dogs showed that a diet containing high fermentable dietary fiber resulted in increased jejunal SGLT1 and Glut2 mRNA abundance (Massimino et al., 1998), but that would not explain enhanced glucose tolerance.

Pea seed coat-supplemented diets significantly enhanced plasma incretin concentrations. GLP-1 has insulinotropic effects and acts directly on pancreatic islets to stimulate insulin secretion from beta-cells, promote beta-cell proliferation and suppress apoptosis (Seino et al., 2010) as well as noninsulinotropic effects such as inhibiting gastric emptying. GLP-1 also inhibits glucagon secretion, and decelerates endogenous production of glucose (Seino et al., 2010). In several animal studies, consumption of fermentable dietary fibres has been linked with elevated plasma GLP-1 (Grover et al., 2011; Wang et al., 2007; Massimino et al., 1998). In addition, in both healthy (Tarini et al., 2010; Johansson et al., 2013) and hyperinsulinemic (Freeland et al., 2010) human subjects, diets high in SDF increased GLP-1 in plasma. In our study, we observed 50% higher fasting GLP-1 in CP group relative to HFD. This could be positive given that it has previously been reported that diabetic patients had significantly lower fasting serum GLP-1 when compared with non-diabetic overweight subjects (Legakis et al., 2003); however, the physiological significance of fasting GLP-1 levels remains elusive. Pannacciulli et al. (2006) examined the association between fasting plasma GLP-1 concentration and energy expenditure and fat oxidation, and reported a positive association between them. In another study, both in-vitro and in-vivo results showed that GLP-1 increased basal uptake of glucose in the muscle through a nitric oxide-dependent pathway, although the concentration of the GLP-1 used was higher than the fasting levels seen in our rats (Chai et al., 2012).

GIP is another incretin that is secreted in response to nutrient ingestion resulting in many similar actions as GLP-1 in the pancreas; however, outside the pancreas, GIP and GLP-1 seem to function differently from one another. GIP secretion has been reported by many studies to be normal or sometimes increased in the state of impaired glucose tolerance and T2D, whereas its insulinotropic effect is diminished in T2D (Kim & Egan, 2008). Studies of the effects of dietary fibre intake on circulating GIP have produced diverse results, with SDF suppressing and IDF augmenting GIP in diabetic and healthy human subjects (Weickert & Pfeiffer, 2008). In healthy adults, a whole barley kernel meal resulted in higher postprandial GIP in plasma (Johansson et al., 2013). In another human study, healthy subjects had lower GIP responses following a whole-kernel rye bread when compared to a white bread meal (Juntunen et al., 2002). In our study, we observed higher GIP responses in the pea fibre-fed rats before and post-glucose ingestion, independent of changes in K-cell number, suggesting increased sensitivity to stimulation. However, because GIP secretion changes were similar in RP and CP, this could not account for the differential effects on oGTT between the groups. Furthermore, improved glucose tolerance could not be accounted for by differences in body weight gain or body fat amongst the groups. In contrast, male Wistar rats, following a high fibre diet (21% wt/wt), composed of inulin and oligufructose, had a lower percentage of body fat (Reimer et al., 2012). In our study, we failed to detect a significant change in body composition, which may be related to the short length of our study (10 weeks) versus that of (21 weeks) Reimer et al (2012).

Finally, the present disclosure demonstrated that HFD supplementation with CP for 4 weeks resulted in almost 50% decrease in beta-cell area in insulin-resistant rats (non-significant). This observation was expected based on the oGTT results suggesting CP-fed rats had an improved glucose tolerance compared with those on the diets supplemented with either RP or cellulose. Given the well-documented beta-cell mass expansion as a major adaptation to insulin resistance (Ahren et al., 2010), the marginal decline in beta-cell mass shown here, in the absence of further elevation in plasma glucose concentrations, could be an indicator of a reversed progression of insulin resistance. A novel finding upon dietary intervention with PSC was the significant difference in alpha-cell mass between groups. Specifically, supplementation with CP decreased alpha-cell mass in glucose-intolerant rats to the level comparable to that seen in the LFD group. While it has been widely asserted that HFD-induced insulin resistance results in expansion in beta-cell area (Goodlad & Mathers, 1992; Pick et al., 1998; Marconi et al., 2000; Hull et al., 2005; Almeida Costa et al, 2006; Ahren et al., 2010), it is not very clear if it has the same impact on alpha-cells. Dysregulated glucagon secretion has been proposed as an early hallmark of type 2 diabetes (D'Alessio, 2011; Liu et al., 2011; Weiss et al., 2011). In diabetic mice increased number of alpha-cells and alpha-cell mass was reported as diabetes developed over time (Liu et al., 2011). In general, it has been suggested that alpha-cell proliferation is regulated by both insulin and glucagon. In response to insulin resistance, elevated intra-islet insulin concentration can originally inhibit glucagon secretion; however, consequently, as alpha-cells develop resistance to insulin, the regulation of glucagon secretion will be impaired. Elevated circulating glucagon then, independent of intra-islet insulin secretion, leads to excessive hepatic glucose production and aggravating hyperglycemia (Liu et al., 2011). In our study, increased alpha-cell area in HFD rats may be due to elevated insulin and glucagon levels in the plasma. At the same time, rats in the CP group had significantly lower plasma insulin concentrations compared to those in the RP and HFD groups, which could explain the smaller alpha-cell area and lower fasting glucagon in that group. In addition, lower glucagon secretion could result in downregulation of hepatic gluconeogenesis and hence reduced fasting plasma glucose concentration. A smaller beta-cell area observed in rats fed CP as compared to those fed RP or cellulose may thus be a result of reduced stress on pancreatic beta-cells.

Current Canadian guidelines (2013) recommend that the diabetic population increase its dietary fibre intake to 25-50 g/day; however, it is not specified what proportion of each fibre type to include. In the present study, rats received 100 grams of pea fibre for almost every 1000 calories consumed, which was approximately 0.05% of their final body weight. This amount corresponds to a daily intake of 35 g fibre in a 70 kg human, which is within the range of the current recommendation of Canadian Diabetes Association for dietary intake in diabetic adults (CDA, 2013). Therefore, incorporating the corresponding amount of pea fibre into human diet may not only be beneficial for improving insulin-sensitivity, but also seems feasible from a practical standpoint.

Example 31: Assessment of a Potential Role of the Gut Microbiome in the Beneficial Effects of Pea Seed Coat-Supplementation on Glucose Homeostasis The following Examples and disclosure demonstrate that cooked pea seed coats elicited greater effects on the gut microbiome and markers of intestinal barrier integrity than raw seed coats.

1. Introduction

Obesity and T2D are among several abnormalities arising in the context of low-grade inflammation (Lee et al., 2013). The gut microbiota is now well established as a modulator of low-grade inflammation caused by elevated circulating levels of LPS, known as metabolic endotoxemia (Cani et al., 2007a; Cani et al., 2009; Muccioli et al., 2010; Shan et al., 2013). Cani and colleagues (2007) were the first to report that exposure to HFD led to elevated levels of LPS (2-3 times higher than normal); following infusion of similar levels of LPS, mice displayed raised glucose and insulin concentrations comparable to those of HFD-fed mice (Cani et al., 2007a). Suppression of TLR-4 signaling, as the main LPS detection pathway, has been shown to improve insulin sensitivity and glucose tolerance in rat models of diet-induced obesity (Liu et al., 2013; Oliveira et al., 2011). In addition, TLR-4 loss-of-function mutant mice demonstrated protection against diet-induced insulin resistance and obesity (Tsukumo et al., 2007). Human studies have also confirmed these results showing that high-fat feeding is associated with increased endotoxin in plasma (Erridge et al., 2007; Pendyala et al., 2012).

Aside from involvement of gut microbiota in metabolic abnormalities due to LPS, further evidence implicating important roles for microbiota in obesity and its related metabolic disorders has been reported. One instance is the report of germ-free mice being protected against diet-induced obesity (Backhed et al., 2007), which was in accordance with a previous study showing that germ-free mice conventionalized with normal microbiota developed features of metabolic diseases including increased fat mass and insulin resistance (Backhed et al., 2004).

In addition, diet-induced obesity is strongly associated with altered gut microbiota composition (Cani et al., 2007; Ley, 2010; Turnbaugh et al., 2006) and impaired gut barrier function recognized by increased intestinal permeability (Cani et al., 2008; De La Serre et al., 2010; Lam et al., 2012). Increased intestinal permeability itself is believed to result from reduced expression of tight junction proteins such as occludin and ZO-1 and their altered pattern of distribution (Everard et al., 2011; Cani et al., 2009).

Given the documented association between gut microbiota and host diet, recent studies have used a dietary approach to induce beneficial changes in the composition of gut microbiota. Dietary probiotics such as inulin and oligofructose are amongst two of the most studied dietary compounds linked with favorable microbial modifying qualities (Bomhof et al., 2014; Bouhnik et al., 2006; Kolida et al., 2007; Parnell & Reimer, 2012). Furthermore, recent evidence suggests that lack of soluble fibre in general contributes to HFD-induced obesity in mice; when compared to HFD with cellulose, inclusion of inulin was shown to protect mice against altered intestinal mass. It was also reported that these changes were associated with increased fecal SCFA production, showing the protective effect of inulin was mediated by gut microbiota (Chassaing et al., 2015). Recently, other types of fermentable dietary fibres including resistant starch, corn-based soluble fibre, wheat dextrin and pea fibre have also been of interest (Boler et al., 2011; Eslinger et al., 2014; Lefranc-Martinez et al., 2010; Millot et al., 2012; Queiroz-Monici et al., 2005). In healthy Wistar rats, peas were shown to possess the strongest bifidogenic properties when compared to other types of pulses including chickpea, bean and lentil (Queiroz-Monici et al., 2005). Another study reported decreased Firmicutes in pea flour- and pea fibre-fed obese rats (Eslinger et al., 2014).

The objective of the present study was to elucidate the effects of feeding glucose intolerant rats PSC fractions on the microbial composition of the gut and select features of gut barrier function, particularly the abundance of TLRs, tight junction and mucin proteins. Since HFD feeding has been associated with adverse microbial modifications in the microbiota, the present inventors hypothesized that dietary supplementation with PSC fractions would alter the overall microbial composition of the gut compared to control diets and it would be associated with the growth of beneficial bacteria such as *Bifidobacterium*. A secondary hypothesis was that PSC-containing diets would partially reverse the HFD-induced changes in intestinal barrier through normalizing the expression of tight junction proteins ZO1 and occludin, toll-like receptors and mucin proteins.

2. Methods 2.1 Animals, Experimental Diets and Tissue Collection

Male Sprague Dawley rats (n=32) were obtained from the Department of Biology, University of Alberta at age eight weeks. During one week of acclimatization, animals were housed two per cage under controlled conditions of temperature and humidity, on a 12-hour light/dark cycle with free access to normal chow and water. The complete composition of the diets and their effects on glucose homeostasis, body weight, body composition and food intake were described in chapter 3. In brief, rats were fed HFD for 6 weeks to induce insulin resistance. They were then randomly assigned to HFD supplemented with either raw (RP) or cooked (CP) pea seed coats. The two control groups were HFD and low fat diet (LFD) with cellulose as the source of dietary fibre, whereas in the RP and CP groups, cellulose was substituted with PSC preparations. Also of note is that all the experimental diets had the same total dietary fibre content. Rats were fed the treatment diets for 4 weeks. They were then anesthetized with ketamine and xylazine and euthanized by exsanguination. Segments of ileum and colon were removed and scrapings were collected along with faecal samples. The animal protocols were approved by the Health Sciences Animal Care and Use Committee at the University of Alberta and conformed to the guidelines of the Canadian Council on Animal Care.

2.2 DNA Extraction and Microbial Profiling

Stool pellets from animals were collected for microbial composition analysis at the time of tissue collection. Total DNA was extracted according to manufacture's instructions (QIAamp DNA Stool Mini kit, Qiagen, Valencia, Calif., USA) with the addition of a 60 s homogenization step (FastPrep instrument, MP Biomedicals, Solon, Ohio, USA). 16S rRNA gene fragments were amplified using a set of 33 nucleotide-bar-coded primer pairs (27F; 5'-AGAGTTTGATCMTGGCTCAG-3' (SEQ ID NO: 9), 519R; 5'-GWATTACCGCGGCKGCTG-3' (SEQ ID NO: 10)) in triplicate. PCR products were then gel-purified with a QiAquick gel extraction kit (Qiagen, Valencia, Calif., USA). The resultant PCR amplicons (100 ng each) were pooled and pyrosequenced with a 454 Titanium platform (Roche, Branford, Conn., USA).

2.2.1 Bioinformatics

Sequences were processed using MOTHUR according to the standard operating procedure, accessed on Jul. 10, 2013 (Schloss et al., 2011). Quality sequences were obtained by removing sequences with ambiguous bases or quality read length less than 200 bases and chimeras identified using chimera.uchime. Quality sequences were aligned to the silva bacterial reference alignment and operational taxonomic units (OTU) were generated using a dissimilarity cutoff of 0.03. Sequences were classified using the classify.seqs command with Ribosomal Database Project (RDP) as reference. Inverse Simpson's diversity index was used to calculate diversity. Differences in microbial communities between groups were investigated using the phylogeny-based weighted UniFrac distance metric. Significant differences in community structure were determined by analysis of molecular variance (AMOVA). Diversity, similarity and abundance of bacterial OTUs and families were compared using the Mann-Whitney U-test or student's t test for nonparametric and parametric data respectively. Bonferroni correction was applied in cases of multiple comparisons.

2.3 RNA Extraction and Real-Time Polymerase Chain Reaction

Total RNA was extracted from ileal and colonic scrapings using Trizol reagent (Invitrogen, Carlsbad, Calif., USA) followed by column-based purification with an RNeasy mini kit (Qiagen, Valencia, Calif., USA) according to the manufacturer's instructions. Reverse transcription was performed on 1 μg of total RNA using a cloned AMV first-strand cDNA synthesis kit (Invitrogen, Carlsbad, Calif., USA). Primers generated by the IBD core at the University of Alberta were used for cDNA amplification by real-time PCR. The sequences of primers are in Table 4-1. Glyceraldehyde-3-phosphate dehydrogenase (GAPDH) was used as the housekeeping gene for normalization of the target genes expression. PCR reactions were performed using Perfecta SYBR green supermix (Quanta BioSciences, Gaithersburg, Md., USA). All assays were run in duplicate on a ViiA™ 7 PCR cycler (Applied Biosystems, Grand Island, N.Y., USA).

2.4 Statistical Analysis

Statistical analyses were conducted using GraphPad Prism 5 (Graphpad Software Inc., La Jolla, Calif., USA). Prior to analyses, data were tested for normality of distribution by the Shapiro-Wilk test. For gene expression data, ΔΔCT analysis was used and statistically significant differences were determined by using one-way ANOVA for parametric and Kruskal-Wallis test for nonparametric data. Bonferroni and Dunn's post-hoc comparison tests were performed as appropriate to assess differences between individual diet groups. Post-hoc tests were corrected for multiple comparisons by the software. All data are expressed as means±SEM and a p-value <0.05 was considered to be significant.

3. Results

3.1 Microbial Community Structure

Figure 13:
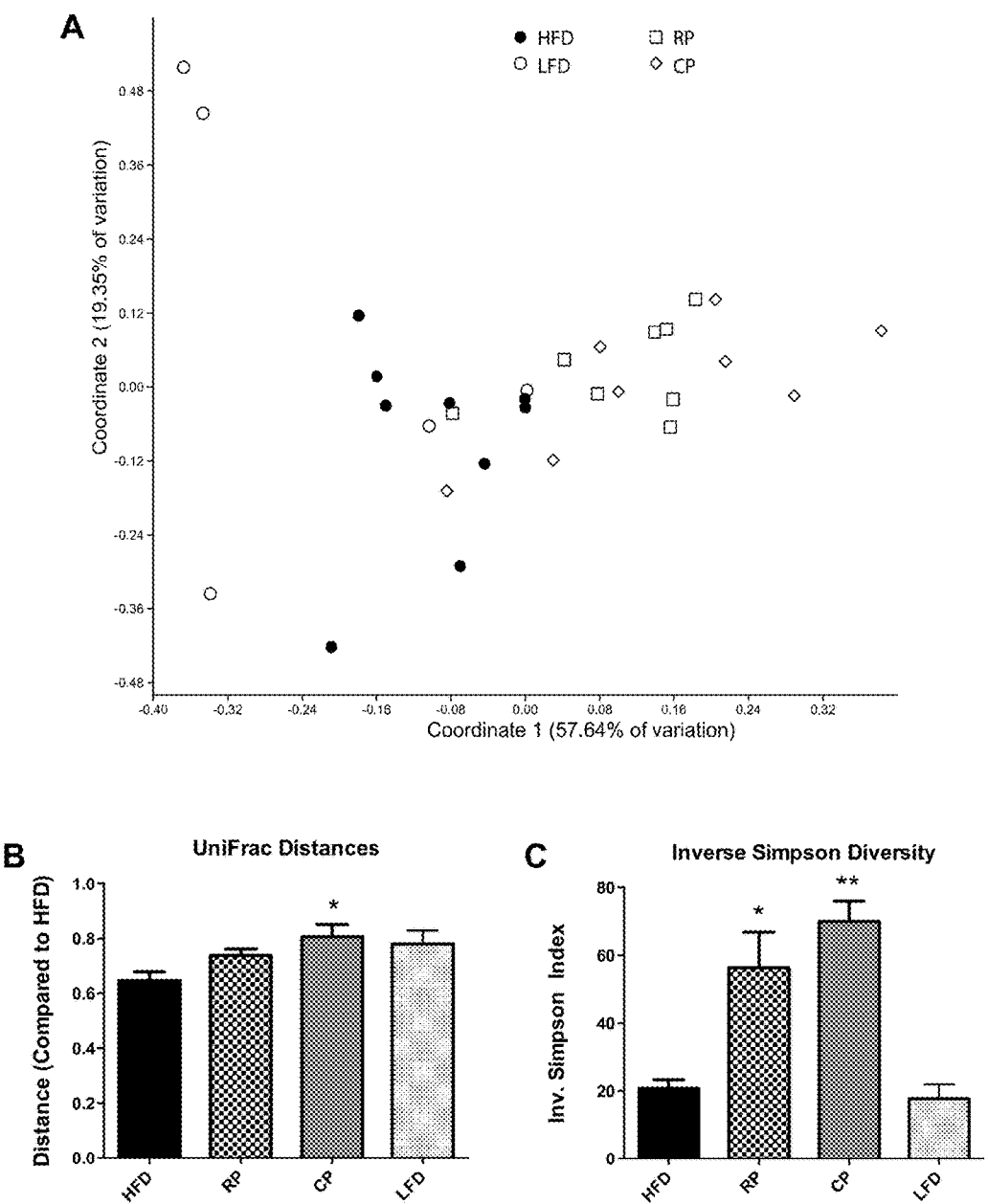
FIG. 13: Effect of feeding PSC on faecal microbial composition. (A) Fecal bacterial communities clustered using PCoA analysis of weighted UniFrac distances, analyzed by AMOVA. The percentage of variation explained by each coordinate is shown in parentheses. (B) Weighted UniFrac distances compared to HFD. (C) Inverse Simpson diversity index as a measure of diversity within each sample. Both UniFrac distances and inverse Simpson diversity indices differed significantly among the groups (P<0.05 and P<0.05). Bars are means±SEM analyzed by one-way ANOVA (B) and Kruskal-Wallis test (C) followed by Bonferroni and Dunn's post-hoc comparison tests (n=6-8); asterisks show significant difference compared to HFD (**P<0.01, *P<0.05).

After quality filtering a mean of 1275±36 sequences were obtained per sample. Addition of RP or CP to the HFD induced a substantial shift in the composition and structure of the faecal microbial community. Grouping of microbial composition by dietary treatment is reflected in the principal coordinate analysis (PCoA) plot in FIG. 13A. Pairwise comparisons of microbial composition by analysis of molecular variance (AMOVA indicated that both CP and RP treatments differed from both HFD and LFD treatment groups (P<0.005), whereas the two PSC treatments did not differ from each other (P=0.179). Unifrac distances of microbial community compared to HFD were significantly different between groups (FIG. 13B, P<0.05). The effects of both RP and CP were very similar, however, only CP revealed a higher mean weighted unifrac distance compared to HFD (P<0.05). While RP and CP differed from HFD, there was no indication that overall community structure became more similar to LFD. As well as showing a shift away from HFD, there was an increase in diversity in response to both RP and CP fractions as indicated by inverse Simpson diversity index (FIG. 13C, P<0.05 and P<0.01 respectively). Again, this did not make CP and RP more similar to LFD as bacterial diversity in LFD and HFD was similar.

At the phylum level, there was an overall increase in the proportion of Firmicutes (P<0.05) and a decrease in the proportion of Bacteroidetes (P<0.05) in CP as compared to HFD. Similar overall patterns were seen with RP, however they did not reach statistical significance (P=0.06 for Bacteroidetes and P=0.12 for Firmicutes). Mean proportion of Firmicutes was 63.9±4.3% in HFD, 71.3±2.2% in RP, 77.4±3.5% in CP and 65.6±3.5% in LFD group and proportion of Bacteroidetes was 34.2±4.2% in HFD, 25.4±1.7% in RP, 19.5±3.2% in CP and 29.6±2.2% in LED rats.

Figure 2:
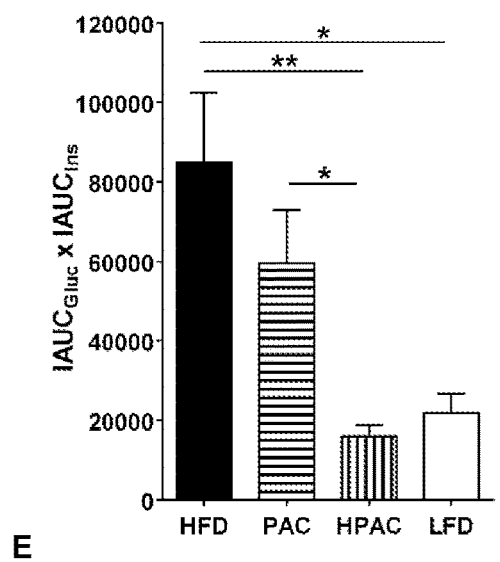
FIG. 2: Blood glucose concentrations and insulin release after glucose challenge in rats fed PAC or HPAC. Intraperitoneal glucose tolerance tests were performed at week 11. After overnight fasting, blood glucose (A) and plasma insulin (B) were measured at 0, 10, 20, 30, 60, 120 min after intraperitoneal administration of 1 g/kg body weight glucose. $^{a}P<0.05$ compared with HFD, $^{b}P<0.05$ compared with LFD, $^{c}P<0.05$ compared with PAC. Incremental area under the curve (IAUC) of glucose response (C) and insulin secretion (D) were calculated from A and B, respectively. (E) Insulin-glucose AUC index calculated from the product of glucose and insulin AUC, where a lower value indicates increased insulin sensitivity (Sutherland et al., 2008; Thrush et al., 2007). HFD, n=11; LFD, n=10; PAC, n=10; HPAC, n=8. *P<0.05, **P<0.01, Bonferroni's multiple comparison.
Figure 14:
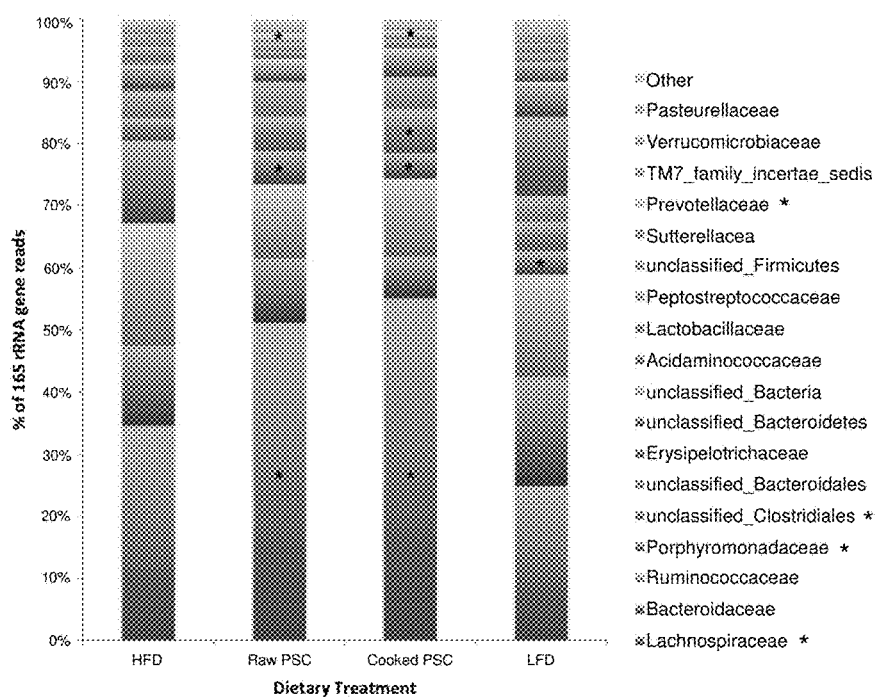
FIG. 14: Microbial taxonomy of faecal samples classified at the family level. Asterisks indicate bacterial families whose population differed significantly compared to HFD (P<0.05 with Bonferonni correction for multiple comparisons), n=6-8.

The effect of dietary treatments on faecal microbial composition at the family level is depicted in FIG. 14. The effects of PSC for the most part did not return the microbial population to that seen in LFD rats. The one exception to that was the population of Porphyromonadaceae. This is the only bacterial family that was affected by PSC the same as LFD, and was the only bacterial family that differed between HFD and LFD. The separation of PSC groups by multivariate analysis was largely associated with the relative proportion of bacteria from the Lachnospiraceae family. Lachnospiraceae was also the most abundant bacterial family in all treatment groups. There was also an increase in Prevotellaceae in RP and CP groups (FIG. 4-2). The pattern of alterations in bacterial populations at all taxonomic levels was very consistent between the two PSC groups, however the CP had a slightly stronger effect on microbial populations, shifting further away from HFD microbiota.

3.2 Gene Expression of TLRs, Tight Junction Proteins and Mucins

Figure 15:
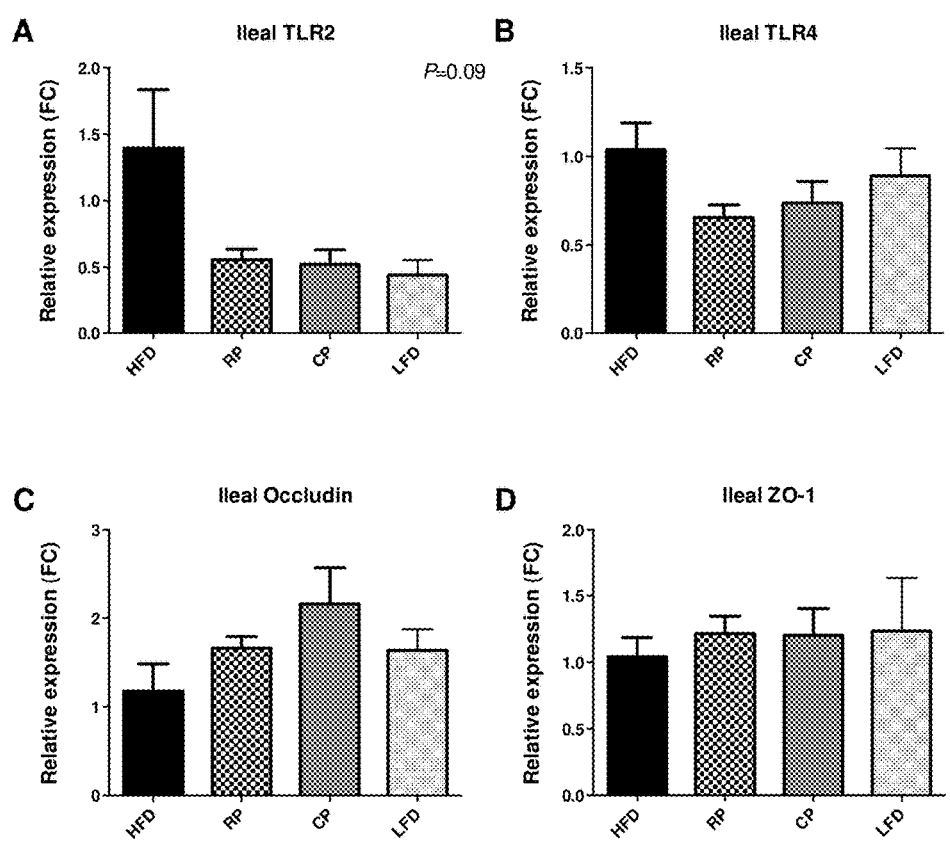
FIG. 15: mRNA expression of TLRs and tight Junction proteins. Mean relative mRNA expression (FC, fold change) of (A) TLR2, (B) TLR4, (C) occludin and (D) ZO-1 in ileum of the rats normalized to GAPDH expression. Data are means±SEM analyzed by one-way ANOVA or Kruskal-Wallis test followed by Bonferroni and Dunn's post-hoc comparison tests as appropriate, n=5-8. No significant differences were found between groups.

Following 4 weeks of feeding experimental diets, ileal expression of TLR2 showed a pattern of elevated expression in HFD relative to other treatments (FIG. 15A, (P=0.09). TLR4 expression did not show the same trend (FIG. 15B, P=0.19). Although not statistically significant, compared to HFD relative expression of TLR2 was decreased by 61% and 63% respectively in the RP and CP rats, which was similar to the LFD rats at 68%. Relative mRNA expression of occludin (84% increase compared to HFD) and ZO-1 in the ileum was numerically highest in CP but did not show significance (FIGS. 15C and D, P=0.16 and P=0.86 respectively).

Figure 16:
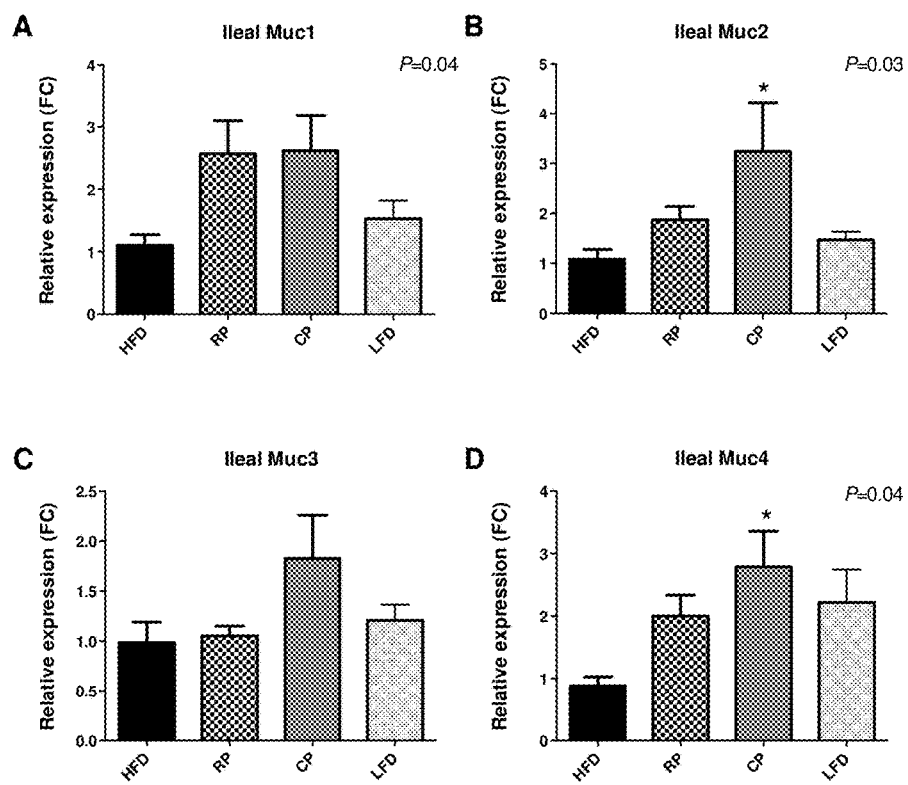
FIG. 16: mRNA expression of mucins. Relative mRNA expression (FC, fold change) of (A) Muc1, (B) Muc2, (C) Muc3 and (D) Muc4 in the ileum. Gene expression data was normalized to GAPDH as the house-keeping gene and presented as means±SEM. One-way ANOVA or Kruskal-Wallis test followed by Bonferroni and Dunn's post-hoc comparison tests as appropriate was used for data analysis, n=6-8. Relative expression of Muc1, Muc2 and Muc4 were significantly different between the groups (P<0.05). CP group showed increased expression of Muc2 and Muc4 genes when compared to HFD group (*P<0.05).

Relative expressions of mucin genes (Muc1, Muc2, Muc3 and Muc4) in the ileum are shown in FIG. 16. After 4 weeks of PSC supplementation, Muc1, Muc2 and Muc4 mRNA expression levels differed between the diet groups (P<0.05). In particular, CP rats showed elevated expression of Muc2 and Muc4 mRNA compared to the HFD group (P<0.05). No significant differences were observed in the ileal expression of Muc3 (FIG. 16C).

4. Discussion

The present study evaluated the effects of PSC feeding on the composition of gut microbiota and markers of intestinal barrier function in HFD-induced glucose intolerant rats. We previously showed that rats fed with PSC-supplemented diets had improved glucose homeostasis compared to a control group fed with HFD containing cellulose (Hashemi et al., 2014). We also observed that enhanced glucose tolerance in the same groups was blunted when the gastrointestinal tract was bypassed during glucose tolerance test. Based on these results, we hypothesized that the mechanisms responsible for the improvement in glucose tolerance in our animal model were, at least in part, mediated by the gut. Specifically, our hypothesis was that PSC supplementation effects on glucose tolerance and insulin resistance would be associated with modified gut microbial composition and enhanced intestinal barrier function.

Firstly, the effects of RP and CP diets were investigated on the overall composition of gut microbiota. Adding PSC to the diet of glucose intolerant rats had the same effect on overall microbial composition whether it was cooked or not. Both RP and CP increased the abundance of Lachnospiraceae, a butyrate-producing family that belongs to the phylum Firmicutes (Vital et al., 2014). This finding is consistent with the present inventors' previous study that indicated an increase in gut-derived 3-hydroxybutyrate with RP inclusion (Chan et al., 2014). Butyrate is one of the three predominant SCFAs generated in the gut, which constitutes the major source of energy for the colonocytes (Bergman, 1990). In addition to serving as an energy substrate, butyrate also acts as a signaling molecule and plays regulatory roles in host metabolism via activation of SCFA receptor FFAR3 (Donohoe et al., 2011; Hara et al., 2014; Lin et al., 2012; Tazoe et al., 2008). Butyrate administration in mice was shown to improve glucose control, increase postprandial levels of GLP-1 and GIP and overall resulted in protection against HFD-induced obesity (Lin et al., 2012). This effect of butyrate on incretin release is consistent with increased basal GLP-1 and GIP secretion in CP rats and enhanced basal and glucose-stimulated GIP secretion in RP group in our study. In addition, there was an increase in Prevotellaceae in both PSC groups, which is in line with a previous animal study showing that inclusion of pectin as the source of fermentable dietary fibre resulted in a 3-23 times increase in the abundance of Prevotellaceae when compared to diets containing arabinoxylan (Ivarsson et al., 2014). In mice, consumption of a diet containing whole grain oats increased the abundance of Prevotellaceae family by 175.5% compared to a low bran oat diet, a change that was also associated with improved insulin sensitivity (Zhou et al., 2015). Furthermore, African children, who consumed diets high in dietary fibre, were found to harbor a large population of the genus *Prevotella*, one of the four genera belonging to the family Prevotellaceae, compared to European children who lacked this bacteria and consumed a typical low-fibre western diet (De Filippo et al., 2010). Likewise, Wu et al. (2011) reported that in adults, dietary fibre intake was associated with a microbiota dominated by *Prevotella*. *Prevotella* species contain bacterial genes that enable them to utilize polysaccharides such as water-soluble xylans (Flint et al., 2012). This was in keeping with fibre analysis data showing that xylose, the primary building block for xylan, was present in both raw and cooked PSC preparations.

The few previous studies that have examined the impact of peas or pea-derived components on the microbial profile of the gut have reported increased *Bifidobacterium* population (Queiroz-Monici et al., 2005), reductions in the abundance of Firmicutes (Eslinger et al., 2014) and substantial changes in the structure of this phylum (Marinangeli et al., 2011); however, these studies were performed under considerably different conditions than disclosed herein. Increased *Bifidobacterium*, for instance, was found following consumption of whole peas supplemented to a balanced diet based on AIN-93G diet. Additionally, those experimental diets were not matched for total dietary fibre and pea diet contained more than double the amount of dietary fibre in the control group (Queiroz-Monici et al., 2005). Eslinger et al. (2014), used commercially available yellow pea-derived components (fibre, starch and flour) as a part of basal diet formulated according to AIN-93M diet with a slightly higher proportion of total dietary fibre (13% wt/wt); the duration of their study (5 weeks of intervention with treatment diets) was also longer than that of ours. Changes in the composition of Firmicutes were reported in hamsters fed untreated commercially available pea flours from whole seeds and seed coats; differences were compared to a control diet containing a lower amount of dietary fibre (Marinangeli et al., 2011). Given that thermal procedures such as boiling, as conducted in our study, can result in partial solubilization and depolymerization of dietary fibre components and alter their functional properties with respect to fermentation, presence or lack of treatment could be partially responsible for differences seen between these studies in terms of microbiota composition. Consistent with the present inventors' results, in the two latter studies, pea fibre-containing diets resulted in lower circulating glucose levels (Eslinger et al., 2014; Marinangeli et al., 2011).

Prebiotics such as inulin and oligofructose have been widely examined for their ability to modulate gut microbiota. Changes in the abundance of *Bifidobacterium* are arguably the most reported microbial outcome at the genus level in prebiotic interventions, both in animals and humans (Bouhnik et al., 2006; Bomhof et al., 2014; Kolida et al., 2007; Parnell & Reimer, 2012; Ramirez-Farias et al., 2009). In the present study however, no *Bifidobacterium* was detected in feces; this might be reflective of housing conditions, a factor known to affect abundance of bifidobacterial populations in mice although at a small magnitude (Thoene- Reineke et al., 2014), or the specific primers used for 16S rRNA gene pyrosequencing. Specifically, some primers have been shown to have limitations in terms of amplification of *Bifidobacterium* species (Palmer et al., 2007). At the phylum level, HFD-induced metabolic disorders including obesity and insulin resistance are sometimes characterized by an increased ratio of Firmicutes to Bacteroidetes (Hildebrandt et al., 2009; Ley et al., 2006; Murphy et al., 2010; Turnbaugh et al., 2006), however, several other studies do not support this link (Duncan et al., 2008; Larsen et al., 2010; Schwiertz et al., 2010; Wu et al., 2010; Zhang et al., 2008). In the present study, an overall significant increase was observed in the proportion of Firmicutes and a reduction in the proportion of Bacteroidetes in CP compared to HFI), whereas RP displayed a similar non-significant pattern. These results are consistent with those of Wu et al. (2011) indicating that dietary fibre consumption was positively linked with increased abundance of Firmicutes in healthy individuals. Considering the inconsistency of reports regarding the Firmicutes to Bacteroidetes ratio, and the fact that these two phyla contain a variety of genera with distinct properties (Eckburg et al., 2005; Haakensen et al., 2008), it is safe to suggest that in order to be more conclusive, interpretation of differences at the level of phylum need to be approached at a more refined level.

The effect of PSC diets on the expression of TLR2 and TLR4 in the ileum were also examined. TLRs are essential for the recognition of microbial components known as pathogen-associated molecular patterns (PAMPs) including LPS, peptidoglycan (PGN), lipoarabinomannan (LAM) and zymosan. While TLR4 recognizes LPS originating from the outer membrane of Gram-negative bacteria, TLR2 is implicated in the recognition of Gram-positive bacterial components such as PGN (Takeuchi & Akira, 2001; McCucker & Kelley, 2013). Upon activation by corresponding PAMPs, TLR2- and TLR4 initiate signaling cascades that eventually result in the production of proinflammatory cytokines, e.g. TNFα and IL-1β (McCucker & Kelley, 2013). It has been shown that inability to respond to LPS through TLR4 protects mice from developing HFD-induced insulin resistance. In addition, HFD feeding resulted in increased expression of TLR2 in adipocytes of insulin resistant mice (Murakami et al., 2007), a finding that corresponds to the presently observed trend toward an increased mRNA expression level of TLR2 in ileal tissue in HFD rats. Another study reported that mice with TLR2 deficiency were protected against HFD-induced insulin resistance (Ehses et al., 2010). Furthermore, patients with newly diagnosed T2D had increased monocyte TLR2 and TLR4 mRNA expression and protein content, a condition that was positively correlated with markers of glucose tolerance such as HOMA-IR, glucose and HbA1c (Dasu et al., 2010). In the present study, both RP and CP groups showed more than 60% reductions in the expression of TLR2 and displayed a trend toward lower levels compared to HFD (P=0.09), suggesting that PSC supplementation was effective in protecting rats from the adverse effects of HFD on TLR2 expression and presumably activation of the downstream signaling pathways. However, a preliminary analysis of the potential effect of these diets on the production of proinflammatory cytokine IL-6 showed no differences in IL-6 gene expression in the ileal mucosa between the treatment groups (data not shown).

To assess evidence for effects of PSC on gut permeability, relative expression of tight junction proteins occludin and ZO-1 was assessed in the ileum. Although not significant, the highest expression levels of occludin (85% above that of HFD) were observed in CP rats, which also had the most enhanced glucose and insulin responses during the oGTT. It is known that in obese mice, metabolic endotoxemia is associated with decreased expression and altered distribution of occludin and ZO-1 (Everard et al., 2011; Cani et al., 2009). The effects of prebiotics on tight junction proteins in models of obesity and obesity-related metabolic disorders have not been reported. However, in a rat model of acute pancreatitis, supplementation with galactooligosaccharides was shown to increase intestinal mRNA levels of occludin, which was linked with improved intestinal barrier function (Zhong et al., 2009). Another study reported increased expression of occludin in healthy rats following supplementation with xylo-oligosaccharide, although the intervention did not result in enhanced intestinal integrity (Christensen et al., 2014). It is important to keep in mind that gene expression data is not an optimal predictor for the functions of tight junction proteins since their organization and distribution plays a more important role in their functionality.

Finally, mRNA levels of mucins in the ileum were examined and significant between-group differences were found for Muc1, Muc2 and Muc4, specifically that CP had higher relative expressions of Muc2 and Muc4 compared to HFD. This finding supports our hypothesis based on the fact that mucins are important for the integrity of mucus layer. In mice, HFD feeding has been associated with changes in the oligosaccharide chains of mucins and consequently their altered composition (Mastrodonato et al., 2014). Consistent with the present results, another animal study also reported decreased expression of duodenal Muc2 following intake of HFD (Schulz et al., 2014). Muc2 is the main structural component of mucus layer, and hence important for the protective function of this layer (Linden et al., 2008). In addition, emerging evidence on the role of mucin-degrading bacteria *Akkermansia muciniphila* in gut barrier function further proves the importance of mucins for the homeostatic actions of mucus layer. Everard et al. (2013) showed that the population of these bacteria was decreased following HFD feeding in mice; the authors continued to demonstrate that administration of oligofructose restored the abundance of *A. muciniphila* and corrected metabolic endotoxemia. Similarly, treatment with viable *A. muciniphila* alongside the HFD abolished metabolic endotoxemia and improved fasting glycemia. While these changes were independent of overall gut microbial composition, they were accompanied by an increase in the mucus layer thickness. The authors concluded that restoration of mucus layer and gut barrier function ameliorated metabolic endotoxemia and improved glycemic control (Everard et al., 2013). The present results on the expression of mucins suggest that PSC-containing diets, especially when cooked, were able to reverse the effect of HFD on mucin expression and potentially benefit the animals with regard to intestinal barrier integrity, which was not directly measured in this study.

There are a few limitations that should be kept in mind when interpreting the present findings. The specific microbiota composition derived from gene pyrosequencing is highly affected by the 16S rRNA regions and primers chosen for amplification (Claesson et al., 2010; Liu et al., 2008). Recognize that gene expression analysis of tight junction proteins is not conclusive without considering the importance of their structure and distribution, which could be modified independently from the abundance of their proteins. Furthermore, it is impossible to infer if changes observed with regard to gut microbial composition were primary or secondary to changes in glucose tolerance in the rats.

5. Conclusion

Overall, the present study demonstrates that inclusion of raw and cooked PSC fractions in diets of glucose intolerant rats alters the composition of gut microbiota, including an increase in one butyrate-producing family. This observation was accompanied by an increased expression of mRNA encoding mucin proteins in the ileum and a trend toward decreased expression of ileal TLR2. These effects, both on microbiota structure and protective gene expression, were consistently stronger in the CP group, which also benefited the most from PSC supplementation in terms of glucose tolerance. These findings suggest a potential protective role for PSC fractions against HFD-induced alterations in the microbial composition of the gut and elements of gut barrier function.

TABLE 4-1

Primer sequences for RT-PCR

| Gene | Sequence (5'-3') |
| --- | --- |
| TLR2 (tlr2, ID 310553) | |
| Forward | GTACGCAGTGAGTGGTGCAAGT (SEQ ID NO: 11) |
| Reverse | GGCCGCGTCATTGTTCTC (SEQ ID NO: 12) |
| TLR4 (tlr4, ID 29260) | |
| Forward | AATCCCTGCATAGAGGTACTTC CTAAT (SEQ ID NO: 13) |
| Reverse | CTCAGATCTAGGTTCTTGGTTG AATAAG (SEQ ID NO: 14) |
| Occludin (ocln, ID 83497) | |
| Forward | ATCTAGAGCCTGGAGCAACG (SEQ ID NO: 15) |
| Reverse | GTCAAGGCTCCCAAGACAAG (SEQ ID NO: 16) |
| ZO-1 (tjp1, ID 292994) | |
| Forward | GCATGTAGACCCAGCAAAGG (SEQ ID NO: 17) |
| Reverse | GGTTTTGTCTCATCATTTCCTCA (SEQ ID NO: 18) |
| Muc1 (muc1, ID 24571) | |
| Forward | TCGACAGGCAATGGCAGTAG (SEQ ID NO: 19) |
| Reverse) | TCTGAGAGCCACCACTACCC (SEQ ID NO: 20) |
| Muc2 (muc2, ID 24572) | |
| Forward | GCACCTTCTTCAGCTGCATG (SEQ ID NO: 21) |
| Reverse | GCGCAGCCATTGTAGGAAAT (SEQ ID NO: 22) |
| Muc3 (muc3, ID 687030) | |
| Forward | CTTGAGGAGGTGTGCAAGAAA (SEQ ID NO: 23) |
| Reverse | CCCCAGGGTGACATACTTTG (SEQ ID NO: 24) |
| Muc4 (muc4, ID 303887) | |
| Forward | GCTTGGACATTTGGTGATCC (SEQ ID NO: 25) |
| Reverse | GCCCGTTGAAGGTGTATTTG (SEQ ID NO: 26) |
| GAPDH (gapdh, ID 24383) | |
| Forward | GTGGCAGTGATGGCATGGAC (SEQ ID NO: 27) |
| Reverse | CAGCACCAGTGGATGCAGGG (SEQ ID NO: 28) |

What is claimed is:

1. A composition comprising an acid hydrolyzed pea seed coat fraction, wherein said acid hydrolyzed pea seed coat fraction is prepared by hydrolysis with a strong acid at a pH of less than 2, and wherein said acid hydrolyzed pea seed coat fraction comprises delphinidin.

2. The composition of claim 1, wherein said acid hydrolyzed pea seed coat fraction further comprises epicatechin and gallocatechin.

3. The composition of claim 1, wherein said acid hydrolyzed pea seed coat fraction is freeze dried.

4. The composition of claim 1, wherein said composition is selected from the group consisting of a food, an animal feed, a flour and a fiber.

5. A method of improving the health of a human or animal comprising administering the composition of claim 1 to said human or animal.

6. The method of claim 5, wherein said improving the health of an animal or human is selected from the group consisting of improving insulin sensitivity, reducing glycemia, increasing satiety, improving glucose tolerance, improving glucose control, improving glucose homeostasis, improving insulin secretion and improving pancreatic islet.

* * * * *

SEQUENCE LISTING

<160> NUMBER OF SEQ ID NOS: 28

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacaccccac tcatagtcac ac                                                22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagcaatgat gagagcatgt g                                                 21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aactttccta gctgcctttg gctc                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tagcaggtgg gaggtcatta agct                                              24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atggtgtggt ggccgattgg                                                   20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgtagatgt ccatggtgaa gag                                               23

```
<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcgatttgt ctggttaatt ccgata                                             26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctaagggcat cacagacctg ttattg                                             26

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agagtttgat cmtggctcag                                                    20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gwattaccgc ggckgctg                                                      18

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtacgcagtg agtggtgcaa gt                                                 22

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggccgcgtca ttgttctc                                                      18
```

```
<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatccctgca tagaggtact tcctaat                                           27

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcagatcta ggttcttggt tgaataag                                          28

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atctagagcc tggagcaacg                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtcaaggctc ccaagacaag                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcatgtagac ccagcaaagg                                                   20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggttttgtct catcatttcc tca                                               23
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcgacaggca atggcagtag                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctgagagcc accactaccc                                                     20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcaccttctt cagctgcatg                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcgcagccat tgtaggaaat                                                     20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttgaggagg tgtgcaagaa a                                                   21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccccagggtg acatactttg                                                     20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcttggacat ttggtgatcc                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcccgttgaa ggtgtatttg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtggcagtga tggcatggac                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagcaccagt ggatgcaggg                                              20
```